United States Patent
Yu et al.

(10) Patent No.: US 8,263,964 B2
(45) Date of Patent: Sep. 11, 2012

(54) THREE-DIMENSIONAL NANODEVICES INCLUDING NANOSTRUCTURES

(75) Inventors: Han Young Yu, Daejeon (KR); Byung Hoon Kim, Incheon (KR); An Soon Kim, Daejeon (KR); In Bok Baek, Cheongju (KR); Chil Seong Ah, Daejeon (KR); Jong Heon Yang, Daejeon (KR); Chan Woo Park, Daejeon (KR); Chang Geun Ahn, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 353 days.

(21) Appl. No.: 12/672,995

(22) PCT Filed: May 19, 2008

(86) PCT No.: PCT/KR2008/002792
§ 371 (c)(1),
(2), (4) Date: Feb. 10, 2010

(87) PCT Pub. No.: WO2009/044983
PCT Pub. Date: Apr. 9, 2009

(65) Prior Publication Data
US 2011/0193052 A1 Aug. 11, 2011

(30) Foreign Application Priority Data
Oct. 5, 2007 (KR) ........................ 10-2007-0100350

(51) Int. Cl.
*H01L 29/06* (2006.01)
(52) U.S. Cl. ............................................ 257/9; 977/762
(58) Field of Classification Search ....... 257/9; 977/762
See application file for complete search history.

(56) References Cited

U.S. PATENT DOCUMENTS
6,529,277 B1 3/2003 Weitekamp
7,207,211 B2 4/2007 Carlson et al.
2007/0023621 A1 2/2007 Blick et al.
2007/0072336 A1* 3/2007 Yu et al. .......................... 438/99
2010/0214034 A1* 8/2010 Peng et al. ..................... 331/154

FOREIGN PATENT DOCUMENTS
KR 1020020035836 A 5/2002
KR 1020050055456 A 6/2005
KR 1020070036355 A 4/2007

OTHER PUBLICATIONS

International Search Report for PCT/KR2008/002792 filed on May 19, 2008.

* cited by examiner

*Primary Examiner* — Thien F Tran

(57) ABSTRACT

Provided are three-dimensional (3D) nanodevices including 3D nanostructures. The 3D nanodevice includes at least one nanostructure, each nanostructure including an oscillation portion floating over a substrate and support portions for supporting both lengthwise end portions of the oscillation portion, supports disposed on the substrate to support the support portions of each of the nanostructures, at least one controller disposed at an upper portion of the substrate, a lower portion of the substrate, or both the upper and lower portions of the substrate to control each of the nanostructures, and a sensing unit disposed on each of the oscillation portions to sense an externally supplied adsorption material. Thus, unlike in a typical planar device, generation of impurities between a nanodevice and a substrate can be reduced, and mechanical vibration can be caused. In particular, since 3D nanostructures have mechanical and electrical characteristics, 3D nanodevices including new 3D nanostructures can be provided using nano-electro-mechanical systems (NEMS). Also, a single electron device, a spin device, or a single electron transistor (SET)-field effect transistor (FET) hybrid device can be formed using a simple process unlike in planar devices.

20 Claims, 17 Drawing Sheets

[Fig. 1]
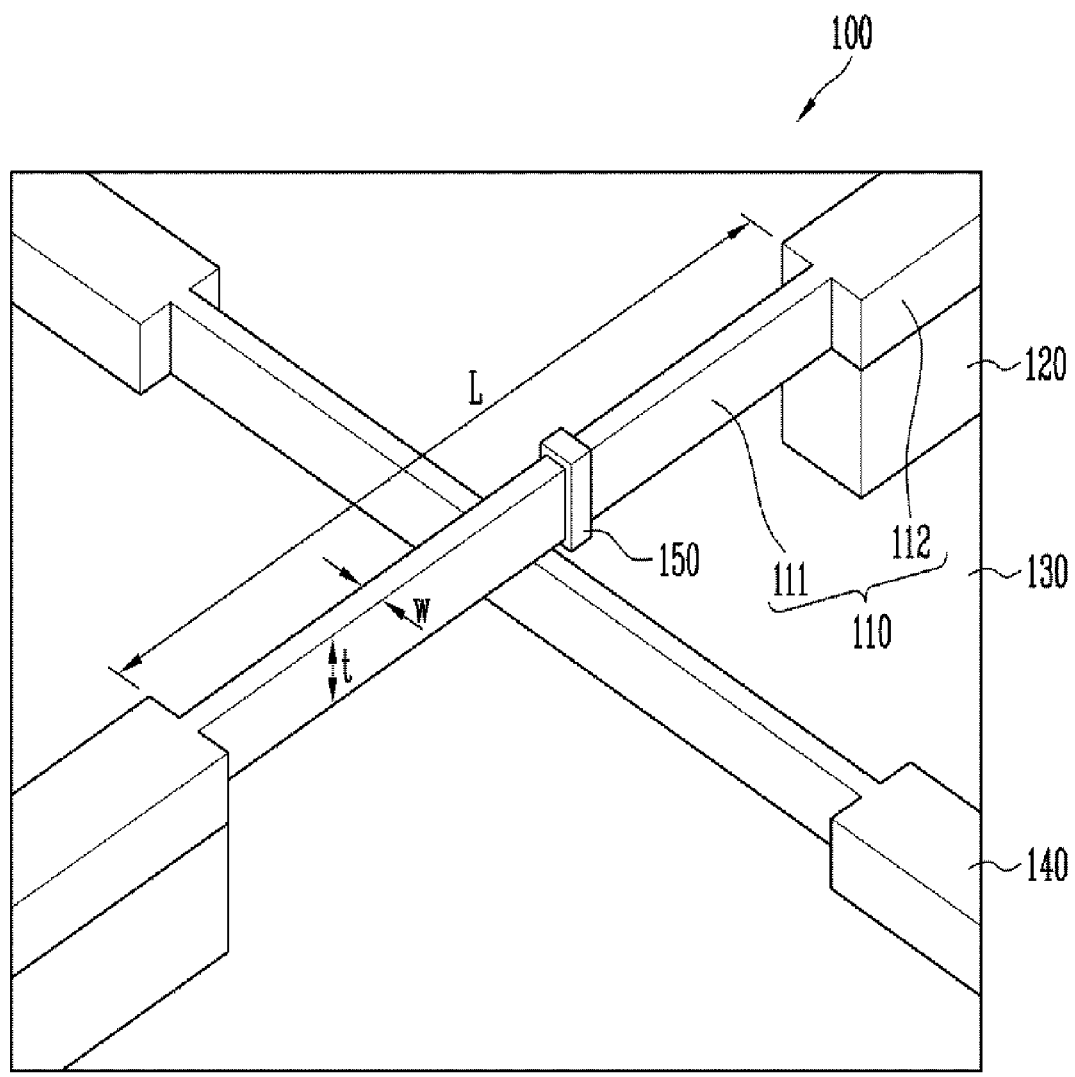

[Fig. 2]
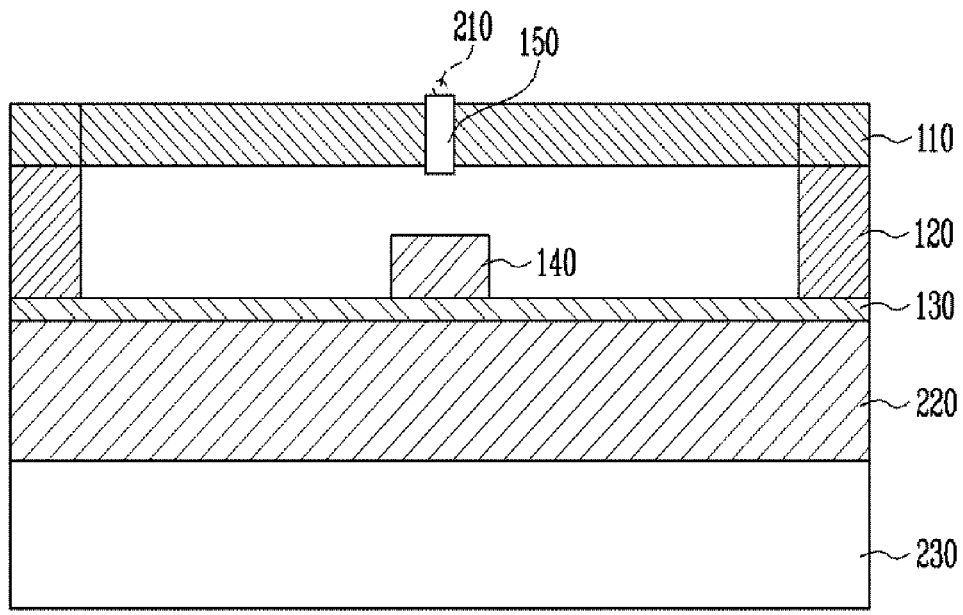
(a)
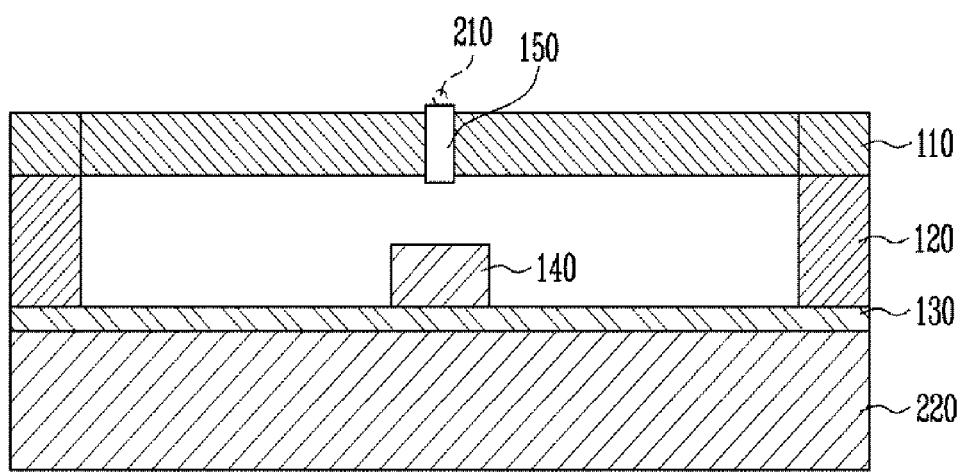
(b)

[Fig. 3]
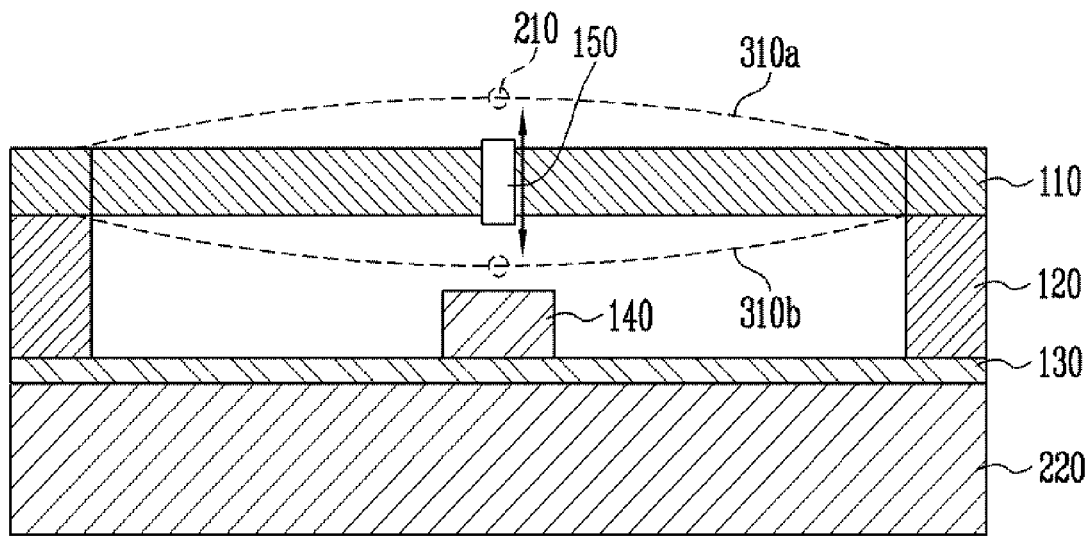
[Fig. 4]
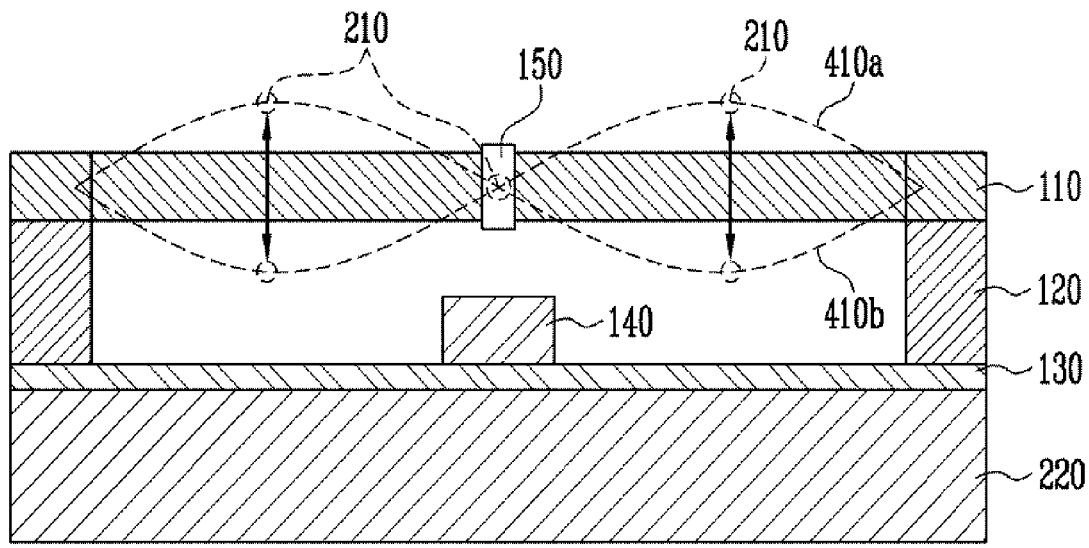

[Fig. 5]
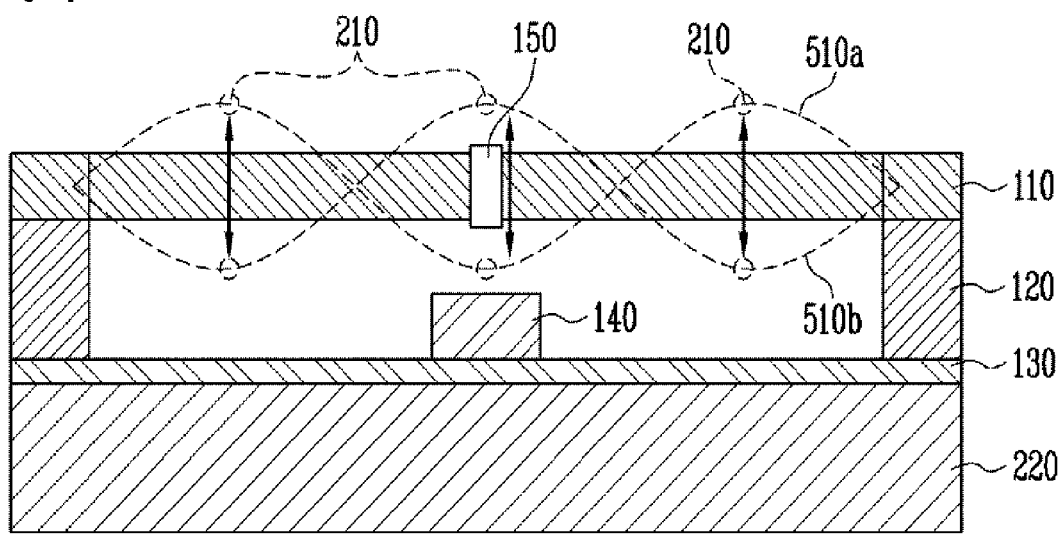

[Fig. 6]
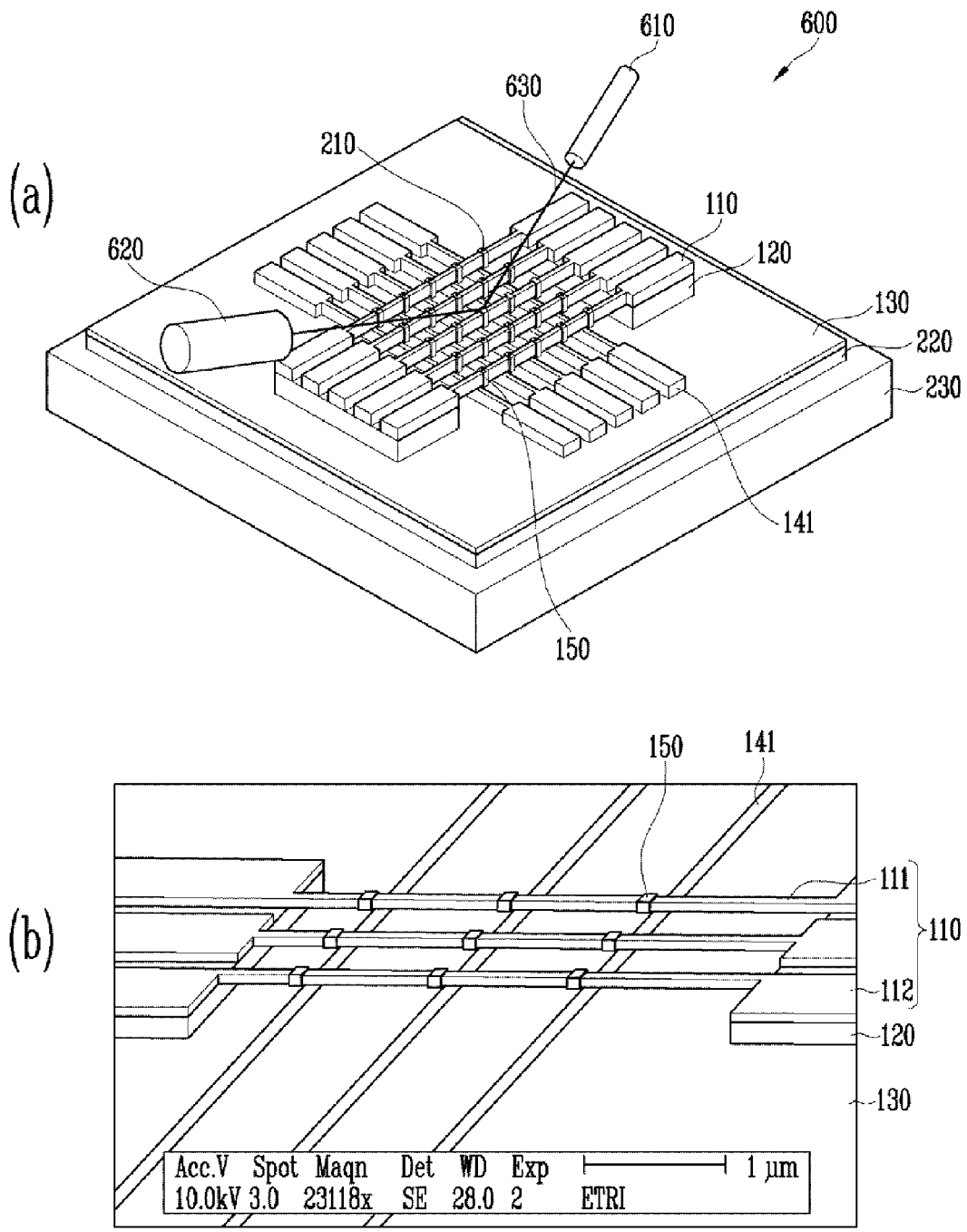

[Fig. 7]
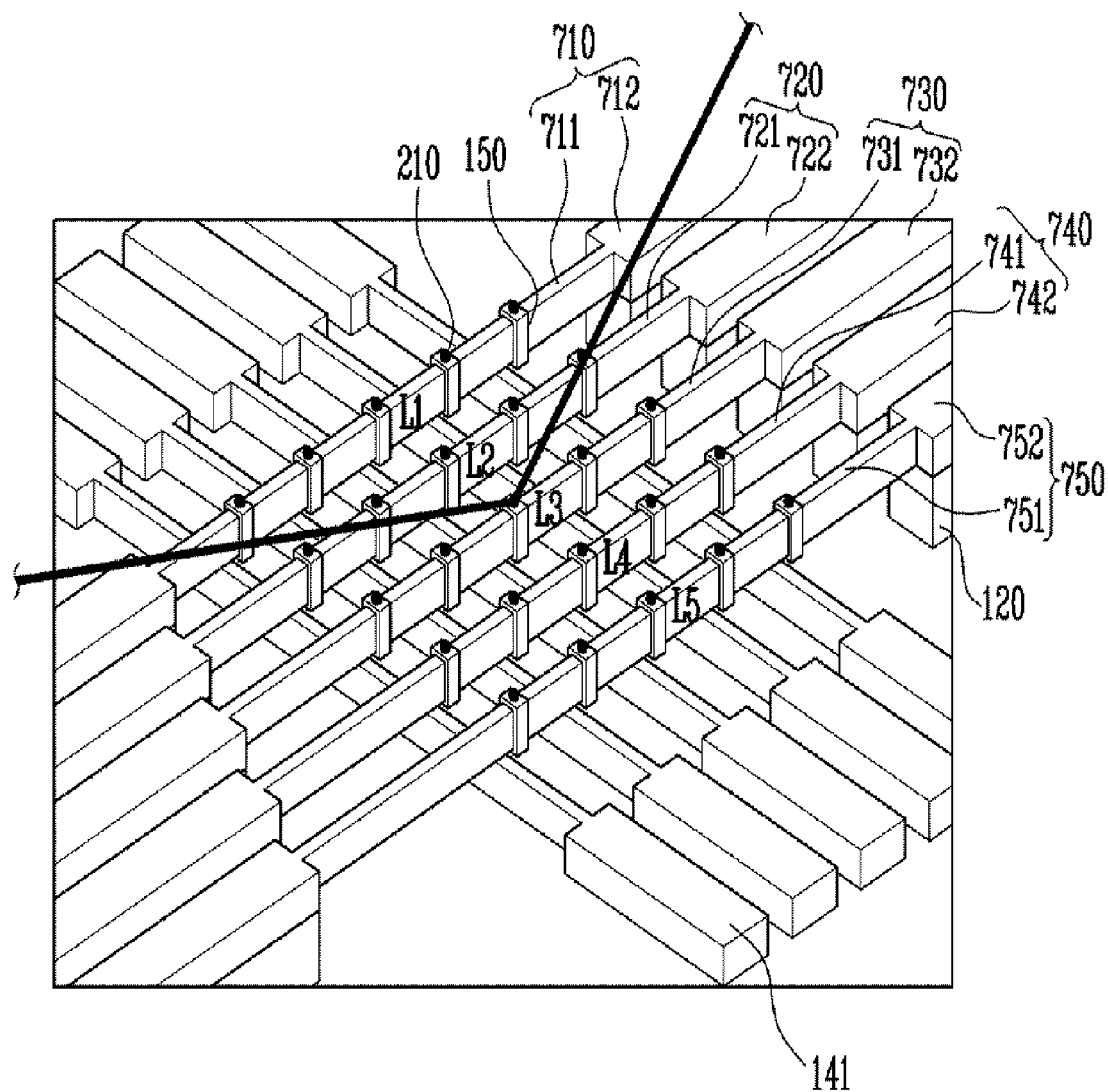

[Fig. 8]
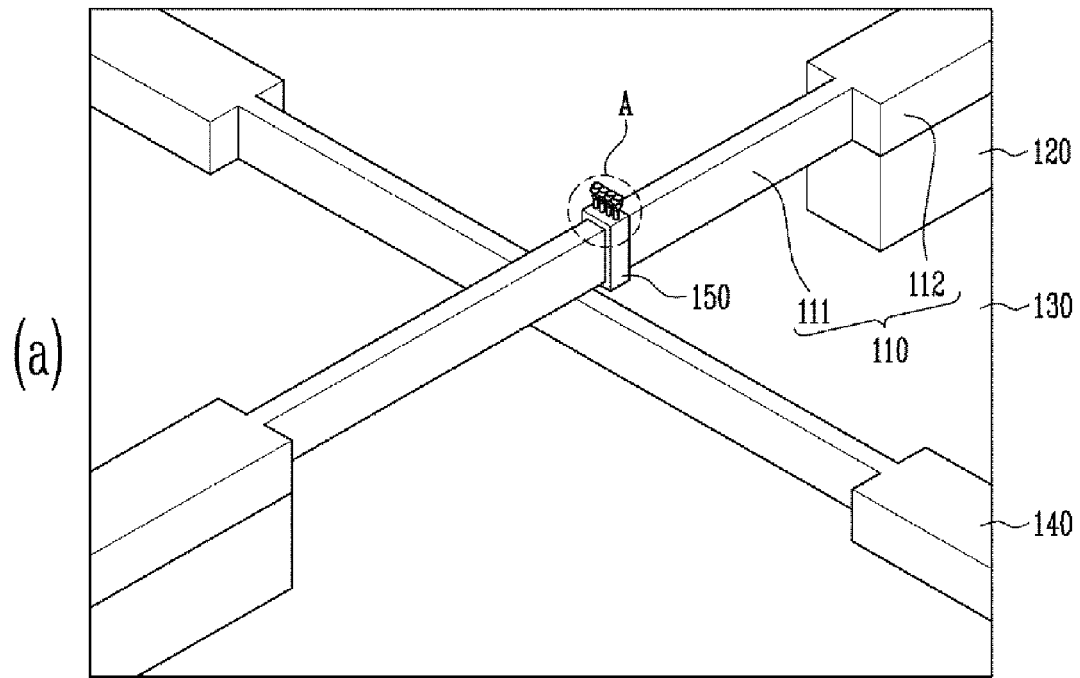
(a)
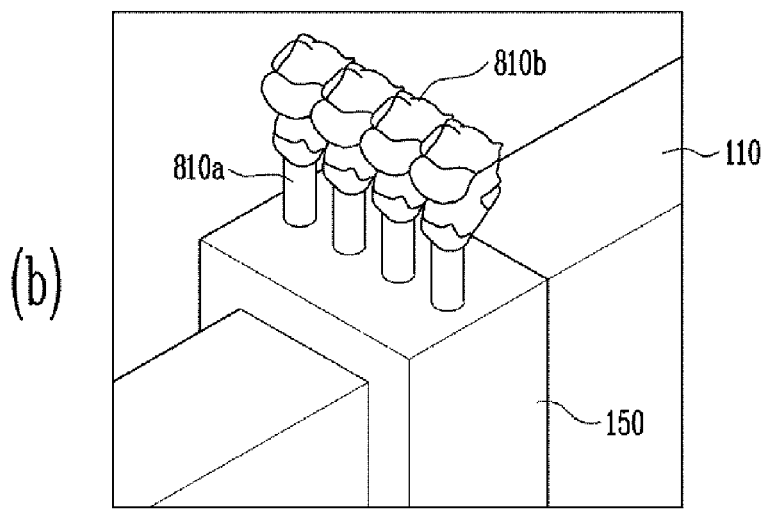
(b)

[Fig. 9]
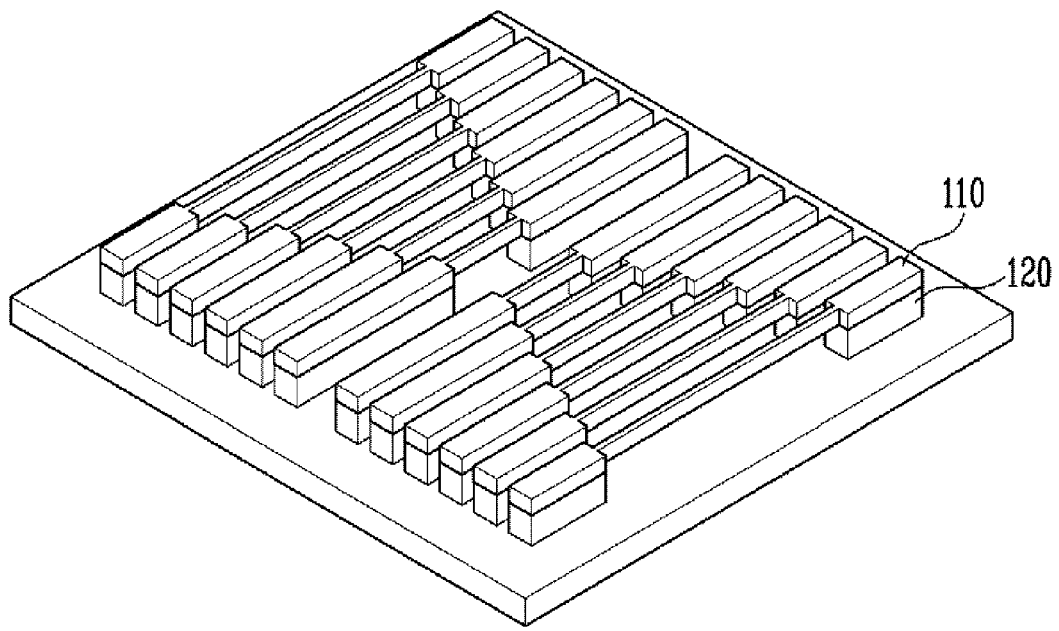
[Fig. 10]
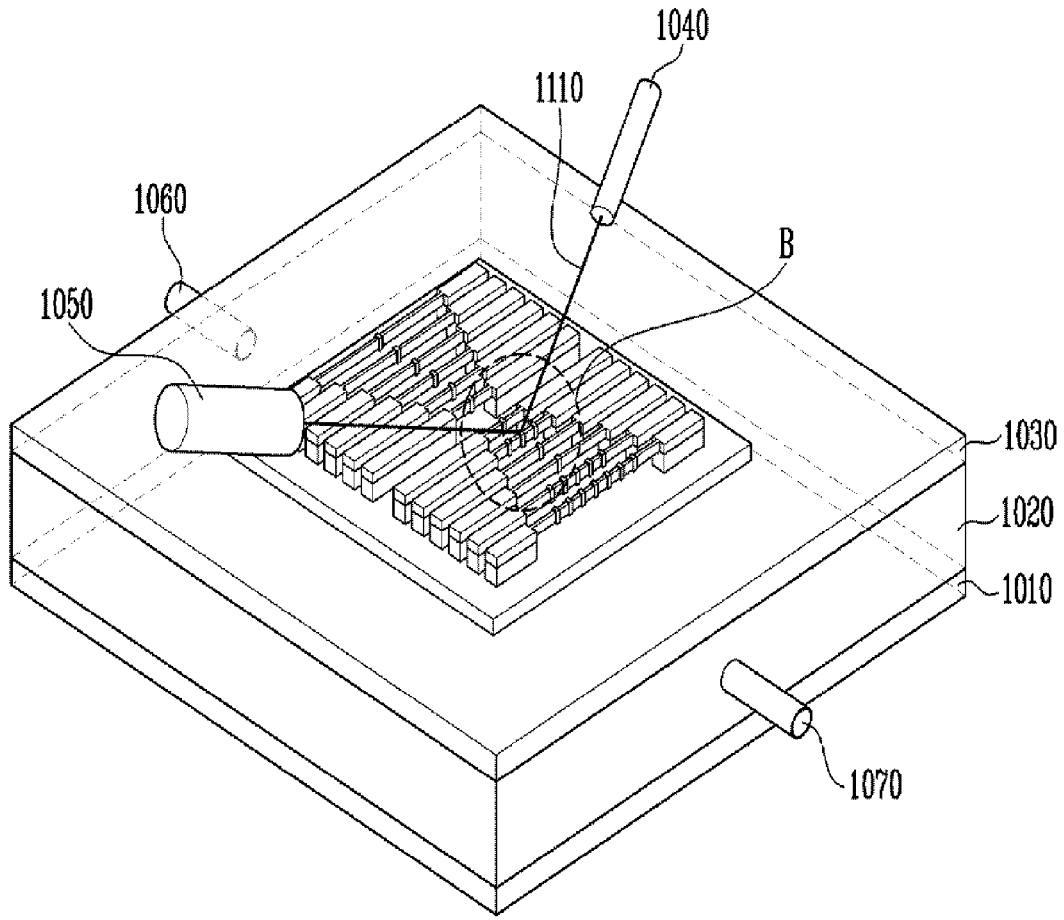

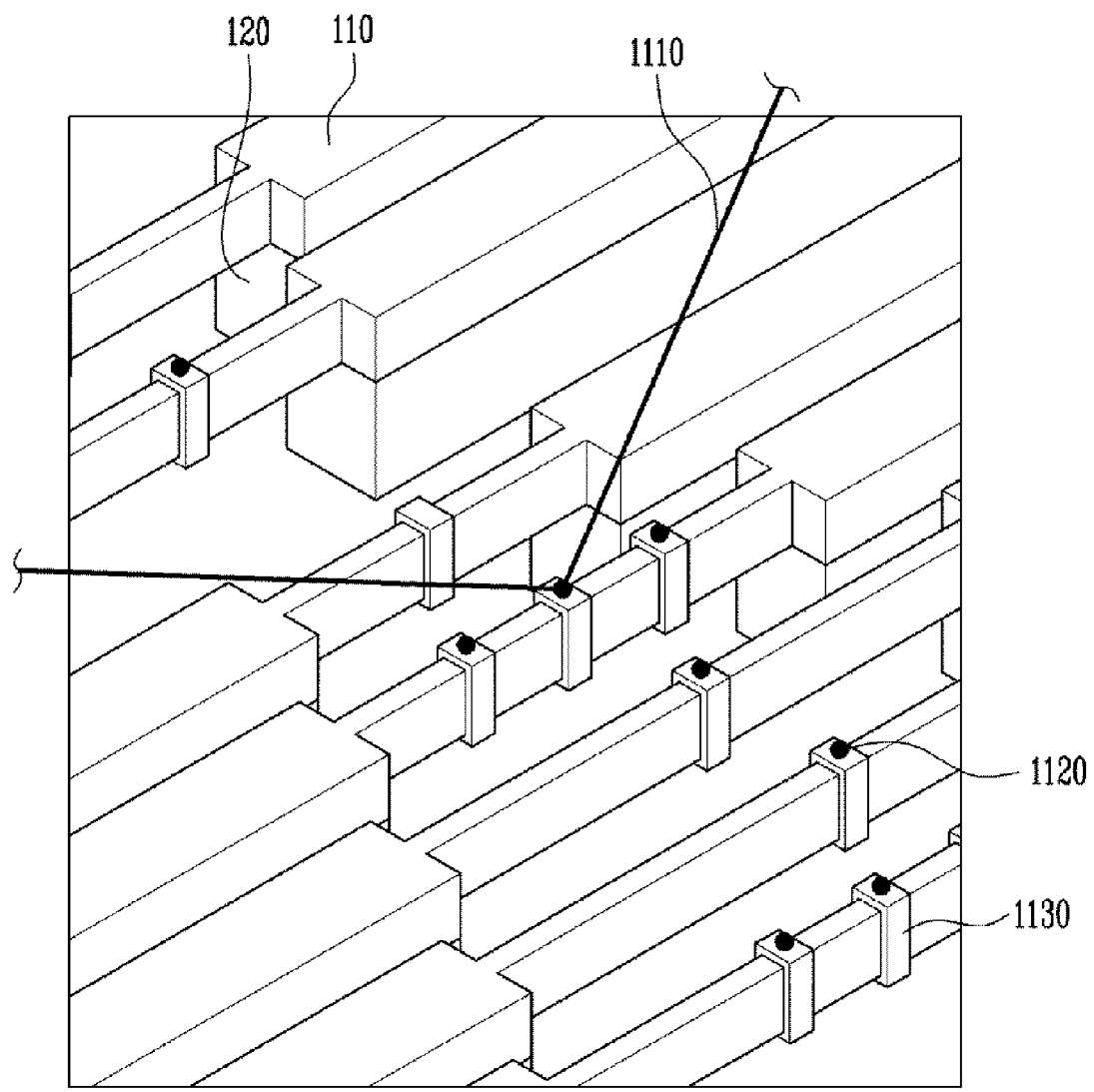
[Fig. 11]

[Fig. 12]
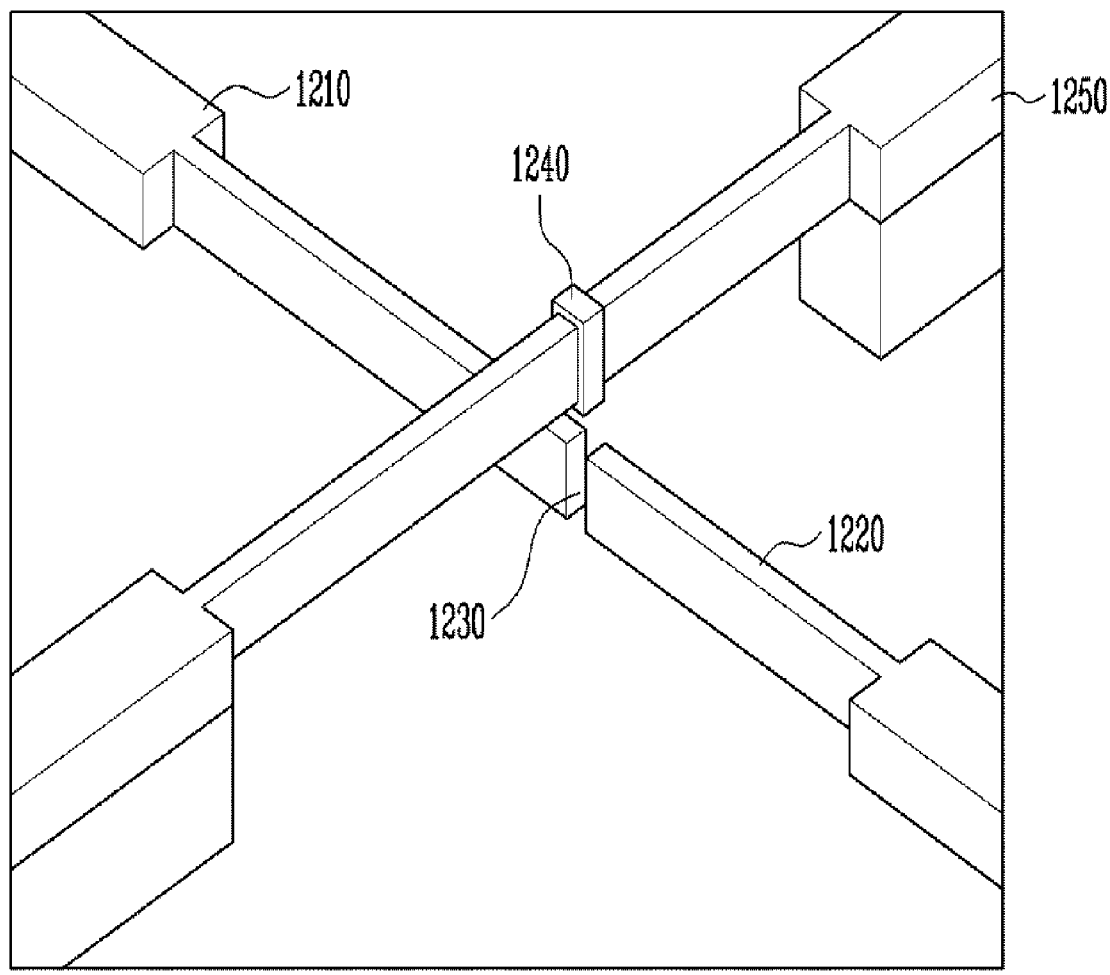

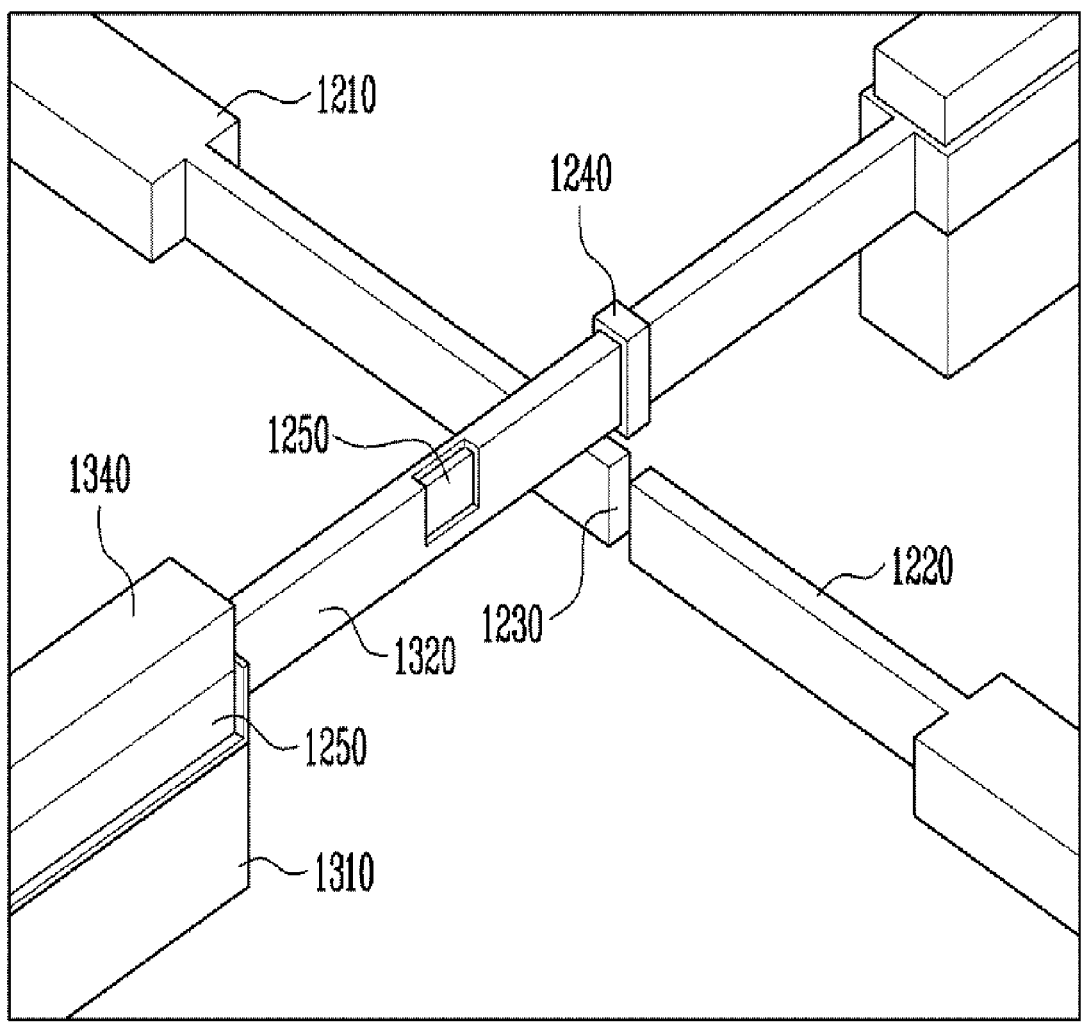
[Fig. 13]

[Fig. 14]
(a)
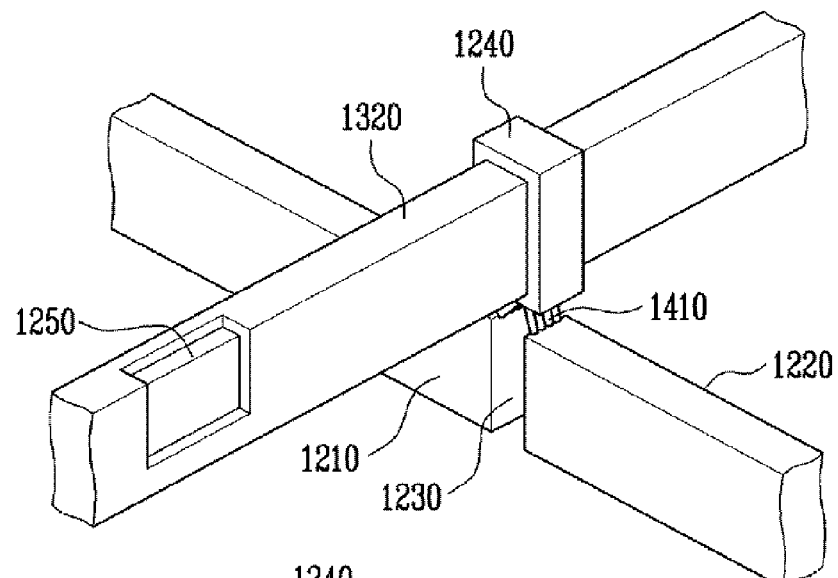
(b)
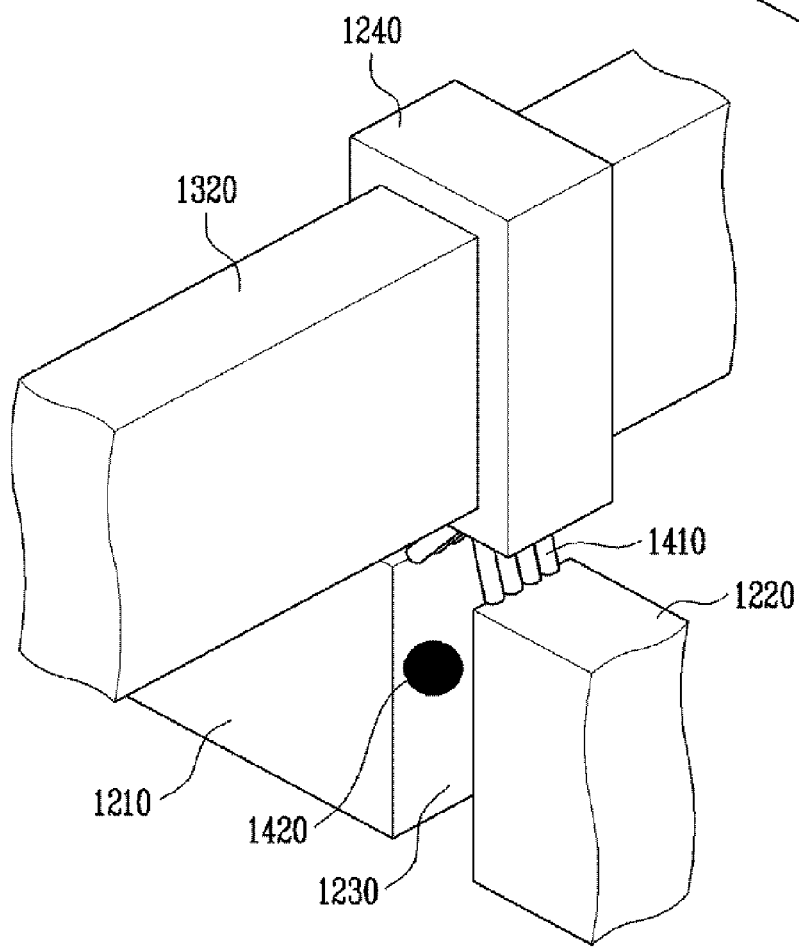

[Fig. 15]
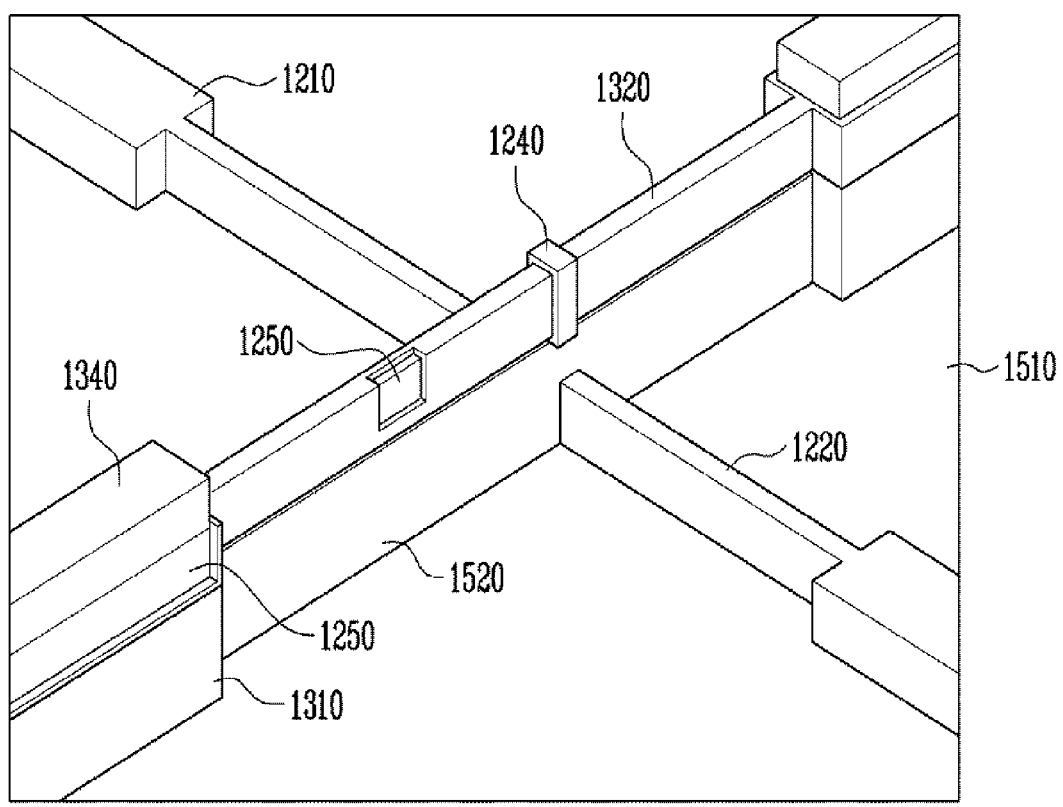

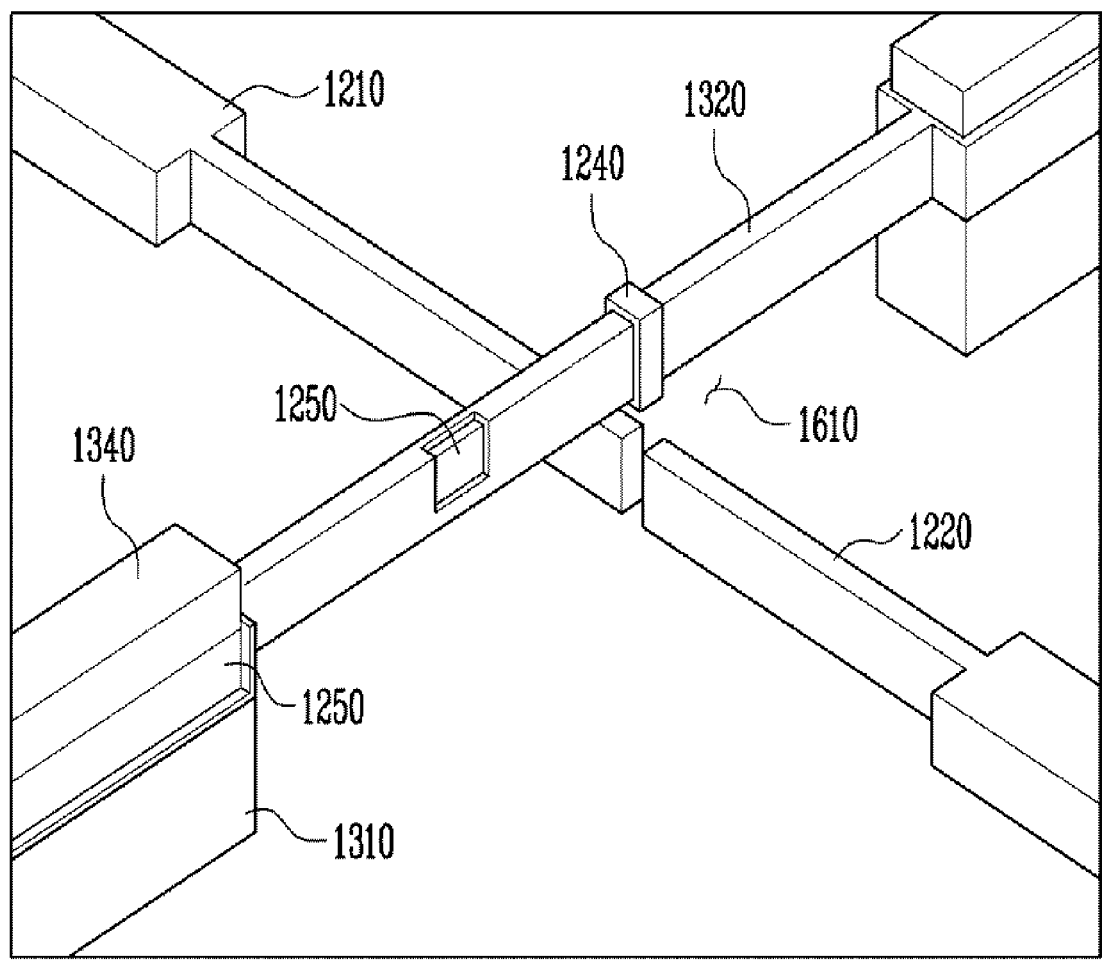
[Fig. 16]

[Fig. 17]
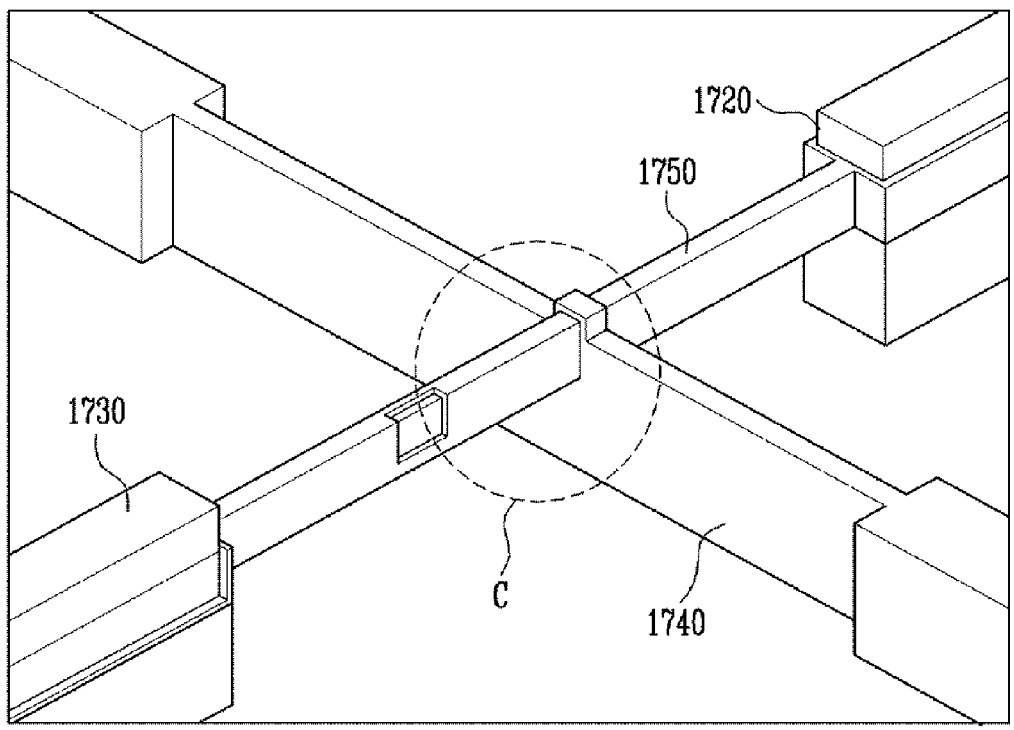
(a)
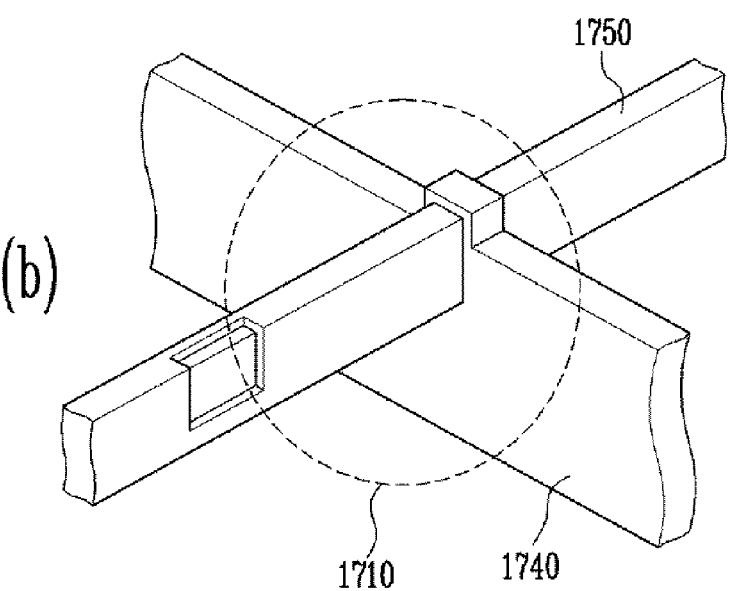
(b)

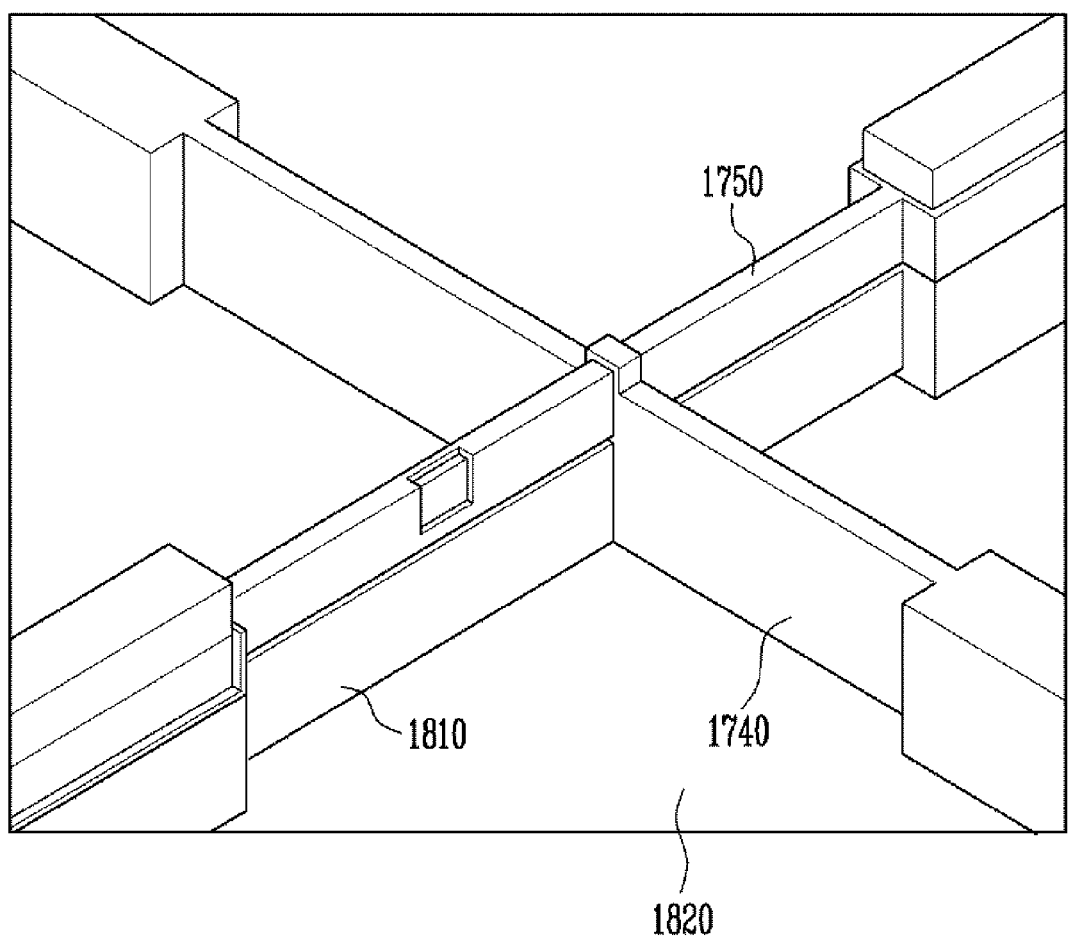
[Fig. 18]

[Fig. 19]
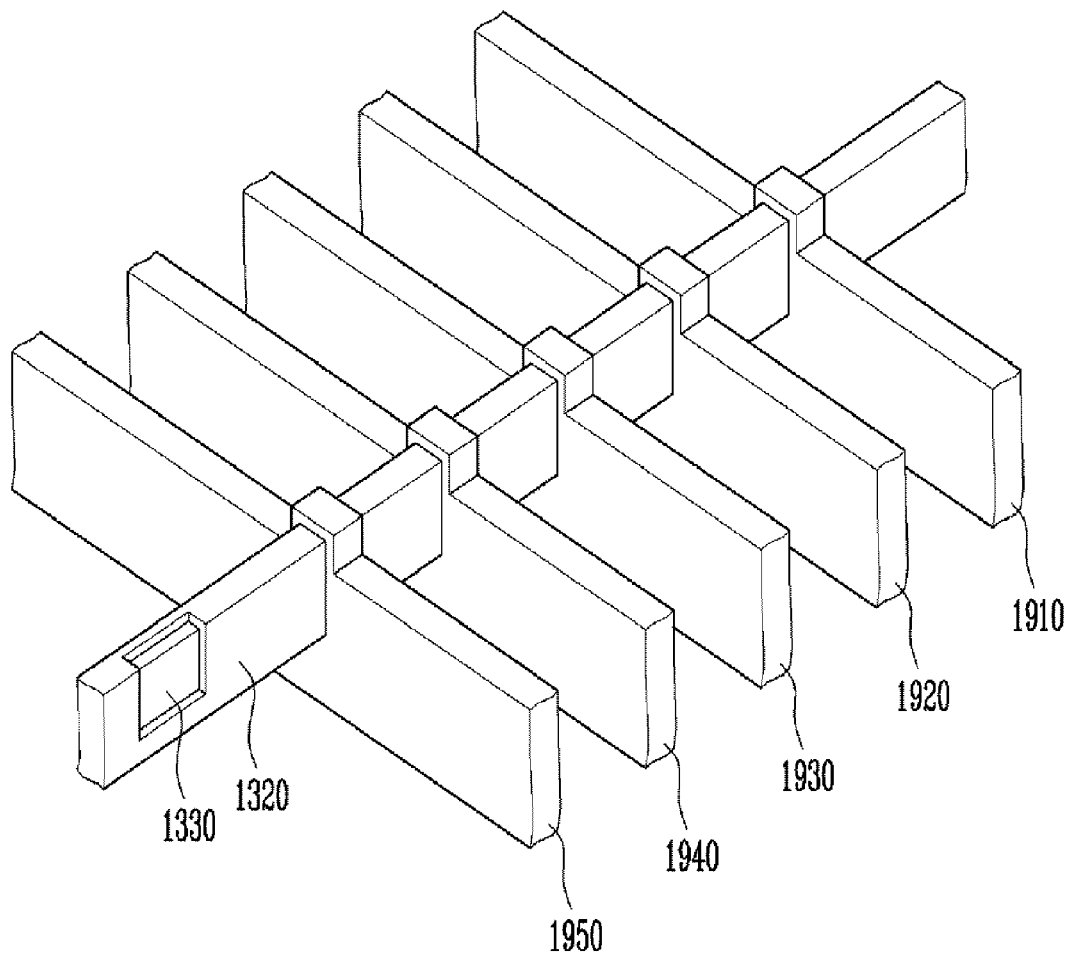
[Fig. 20]
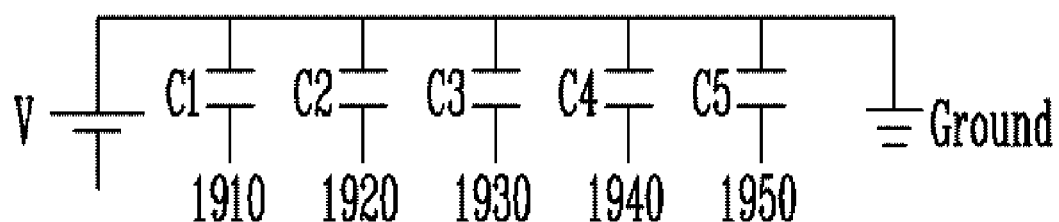

THREE-DIMENSIONAL NANODEVICES INCLUDING NANOSTRUCTURES

TECHNICAL FIELD

The present invention relates to three-dimensional (3D) nanodevices, and more particularly, to 3D nanodevices including 3D nanostructures, which can be applied in more various shapes and fields, as compared with conventional two-dimensional (2D) nanodevices.

Also, the present invention relates to 3D nanodevices, which overcome the applicable restrictions of 2D devices, reduce noise due to the sensing of electrical signals by detecting optical signals, and sensing signal can be enhanced by using additional electrical effects.

BACKGROUND ART

With the development of information and communication technologies, the amount of data that can be transmitted has increased in geometrical progression, and the integration density of semiconductor devices for processing the data has also gradually increased.

However, the integration density of most semiconductor devices depends on equipment for embodying the semiconductor devices, and a method of miniaturizing the semiconductor devices also depends on the properties of the equipment. Also, there is a specific technical limit for applying miniaturized semiconductor devices to new driving devices, such as sensors and other bio-material sensing devices.

DISCLOSURE OF INVENTION

Technical Problem

The present invention is directed to three-dimensional (3D) nanodevices having new structures and better electrical properties than two-dimensional (2D) nanodevices, wherein an electrical device and an optical device are complementary to each other.

Also, the present invention is directed to 3D nanodevices, which function not only as active drivers (e.g., transistors) for electric devices but also as sensors.

Furthermore, the present invention is directed to 3D nanodevices, which function as quantum devices for providing quantum mechanical vibration.

Technical Solution

One aspect of the present invention provides a 3D nanodevice including: at least one nanostructure, each nanostructure including an oscillation portion floating over a substrate and support portions for supporting both lengthwise end portions of the oscillation portion; supports disposed on the substrate to support the support portions of each of the nanostructures; at least one controller disposed at an upper portion of the substrate, a lower portion of the substrate, or both the upper and lower portions of the substrate to control each of the nanostructures; and a sensing unit disposed on each of the oscillation portions to sense an externally supplied adsorption material.

The 3D nanodevice may further include an external oscillation portion disposed under the substrate. The controller may include a piezoelectric material or a metal material, which is disposed at a lower portion and/or an upper portion of the oscillation portion of the nanostructure to intersect the nanostructure and cause oscillation of the oscillation portion.

Also, the controller may include at least one electrode, which is disposed under the oscillation portion over the substrate to intersect the nanostructure and cause oscillation of the oscillation portion.

The oscillation portion may have a width of several nm to 1 μm, a height of several nm to 1 μm, and a length of 100 nm to 100 μm. Each of the oscillation portion and the substrate may be formed of one selected from the group consisting of Si, Ge, Sn, Se, Te, B, C, P, B—C, B—P(BP6), B—Si, Si—C, Si—Ge, Si—Sn, Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, $BeSiN_2$, $CaCN_2ZnGeP_2$, $CdSnAs_2$, $ZnSnSb_2$, $CuGeP_3$, $CuSi_2P_3$, $(Cu, Ag)(Al, Ga, In, Ti, Fe)(S, Se, Te)_2$, $SiO_2$, $Si_3N_4$, $Ge_3N_4$, $Al_2O_3$, $(Al, Ga, In)_2(S, Se, Te)_3$, $Al_2CO$, and combinations thereof.

A plurality of nanostructures may be formed. In this case, the oscillation portions of the nanostructures may have the same length. Alternatively, at least some of the oscillation portions of the nanostructures may have different lengths. The oscillation portion may use resonance and nonlinear frequencies according to the length thereof. The sensing unit may be formed at a maximum-amplitude region of the resonance frequency, and a probe for adsorbing a material may be formed at the maximum-amplitude region. The sensing unit may be formed of metal, silicon, or oxide. An organic probe may be disposed on the sensing unit. The organic probe may be chemically combined with the supplied material and formed of at least one selected from the group consisting of a thiol group, an amine group, a silane group, DNA combined with at least one of the thiol group, the amine group, and the silane group, and a bio-material containing an antibody.

The 3D nanodevice may further include: a lateral portion formed along a circumference of the substrate; a fluid inlet port disposed in a first region of the lateral portion; a fluid outlet port disposed in a second region of the lateral portion; and a top portion disposed on the lateral portion.

The 3D nanodevice may further include: a laser unit for irradiating laser beams to the oscillation portion of the nanostructure; and a laser sensing unit for receiving the laser beams from the laser unit.

Another aspect of the present invention provides a three-dimensional nanodevice including: at least one nanostructure, each nanostructure including an oscillation portion floating over a substrate and support portions for supporting both lengthwise end portions of the oscillation portion; supports disposed on the substrate to support the support portions of the nanostructure; at least one electrode disposed under the oscillation portion of the nanostructure to intersect the nanostructure; and a sensing unit disposed on the oscillation portion to sense an externally supplied adsorption material.

The electrode may include a source electrode and a drain electrode, and a gap may be formed between the source and drain electrodes. A quantum dot may be formed in the nanostructure over the gap formed between the source and drain electrodes. Also, the source and drain electrodes may be formed of a magnetic material. A plurality of gates may be disposed over the substrate.

Advantageous Effects

According to the present invention as described above, 3D nanodevices such as mass spectrometers and electronic devices can be easily manufactured by forming 3D nanostructures. Since the nanodevices manufactured using the 3D nanostructures include oscillators with high sensitivities, they can be used as sensors for measuring fine molecular mass (e.g., bio-molecular mass). Furthermore, according to the present invention, 3D electronic devices having various shapes can be manufactured by forming gate electrodes using simple processes.

BRIEF DESCRIPTION OF THE DRAWINGS

FIG. 1 is a partial perspective view of a mass spectrometer including a nanostructure according to an exemplary embodiment of the present invention;

FIG. 2A is a cross-sectional view of a mass spectrometer including an external oscillation portion disposed under a substrate;

FIG. 2B is a cross-sectional view of a mass spectrometer in which an external oscillation portion is not disposed under a substrate;

FIGS. 3 through 5 are cross-sectional views of the mass spectrometer shown in FIG. 1, wherein an oscillation portion enters an oscillation mode to sense a mass variation;

FIG. 6A is a perspective view of a three-dimensional (3D) sensor including a plurality of nanostructures and a laser sensing unit according to another exemplary embodiment of the present invention;

FIG. 6B is a partial scanning electron microscope (SEM) image of the 3D sensor shown in FIG. 6A;

FIG. 7 is a schematic diagram of a plurality of nanostructures including oscillation portions with different lengths;

FIG. 8A is a schematic diagram of a molecular sensor using nanostructures according to an exemplary embodiment of the present invention;

FIG. 8B is an enlarged view of region "A" shown in FIG. 8A;

FIG. 9 illustrates the layout of a plurality of nanostructures including oscillation portions with different lengths;

FIG. 10 is a view showing the construction of a sensor in the fluidic using the nanostructures shown in FIG. 9;

FIG. 11 is an enlarged view of region "B" shown in FIG. 10;

FIG. 12 is a diagram of a single electron transistor (SET) using nanostructures according to another exemplary embodiment of the present invention;

FIG. 13 is a diagram of a 3D electronic device according to another exemplary embodiment of the present invention, which performs operations more actively than the SET shown in FIG. 12;

FIG. 14A is a view showing the construction of a 3D electronic device according to another exemplary embodiment of the present invention, wherein a molecular insulating layer or an organic insulating layer is deposited without using air and vacuum as tunneling potentials as in FIGS. 12 and 13;

FIG. 14B is a view showing the construction of a 3D electronic device according to another exemplary embodiment of the present invention, wherein a transistor is driven by attaching a molecular and organic material or a nanodot material to at least a region of a gap formed between a source electrode and a drain electrode;

FIGS. 15 and 16 are views showing the constructions of a SET, a spin device, or a field-effect transistor (FET), which includes nanostructures, according to exemplary embodiments of the present invention;

FIG. 17A is a view showing the construction of a FET using air or a vacuum state as an insulating layer, according to another exemplary embodiment of the present invention;

FIG. 17B is an enlarged view of region "C" shown in FIG. 17A;

FIG. 18 is a view showing the construction of a FET for a molecular spin device according to an exemplary embodiment of the present invention, wherein an insulating layer is formed of an inorganic material;

FIG. 19 is a view showing the construction of a SET including a plurality of gates using an electric field; and FIG. 20 is a circuit diagram of the SET shown in FIG. 19.

DESCRIPTION OF MAJOR SYMBOLS IN THE ABOVE FIGURES

110: Nanostructure
111: Oscillation portion
112: Support portion
120: Support of the nanostructure
130: Insulating layer
140: Controller
150: Sensing unit
210: Adsorbed material
220: Substrate
230: External oscillation portion (PZT)
310a, 310b: Amplitude displacement
410a, 410b: Amplitude displacement
510a, 510b: Amplitude displacement
610: Laser source
620: Laser sensing unit
630: Laser
710, 720, 730, 740, 750: Nanostructures having oscillation portions of different lengths
810a: Probe
810b: Bio material probe
1010: Bottom portion
1020: Lateral portion
1030: Top portion
1040: Laser
1050: Laser sensing unit
1060: Fluid inlet port
1070: Fluid outlet port
1110: Laser source
1120: Adsorbed material
1130: Sensing unit
1210: Source electrode
1220: Drain electrode
1230: Gap
1240: Quantum dot (Nano dot)
1250: Nanostructure (Top gate)
1310: Support
1320: Gate insulating layer
1330: Channel
1340: Electrode
1410: Organic or molecular gate insulating layer
1420: Organic material or metal nano particle or organic channel
1510: Insulating layer
1520: Gate insulating layer
1610: Gate insulating layer
1910, 1920, 1930, 1940, 1950: Gate

Mode for the Invention

The present invention provides three-dimensional (3D) nanodevices, each nanodevice including a substrate for supporting the nanodevice and 3D nanostructures. Also, the substrate is isolated from active devices by a dielectric material layer. The structure of the 3D nanodevices may be varied according to purposes, but in general the 3D nanostructures are floated over a two-dimensional (2D) substrate. Variations of the 3D nanodevice will be described more fully hereinafter with reference to the accompanying drawings, in which exemplary embodiments of the invention are shown.

Embodiment 1: Mass Spectrometer and Sensor

FIG. 1 is a partial perspective view of a mass spectrometer including a nanostructure according to an exemplary embodiment of the present invention, FIG. 2A is a cross-sectional view of a mass spectrometer including an external oscillation portion disposed under a substrate, and FIG. 2B is a cross-sectional view of a mass spectrometer in which an external oscillation portion is not disposed under a substrate.

Referring to FIGS. 1, 2A, and 2B, a mass spectrometer 100 includes a substrate 220, an insulating layer 130 disposed on the substrate 220, a nanostructure 110 installed to float over the substrate 220, a support 120 prepared on the substrate 220 to support both lengthwise ends of the nanostructure 110, a sensing unit 150, which is prepared on the nanostructure 110 and adsorbs a material 210 flowing into the mass spectrometer 100 to sense variations in mass and electric and magnetic fields of the adsorbed material 210, and a controller 140 prepared on the insulating layer 130 to control the sensing unit 150.

The nanostructure 110 includes a linear oscillation portion 111, which is three-dimensionally floated over the insulating layer 130 disposed on the substrate 220, and support portions 112 disposed on both ends of the oscillation portion 111. The sensing unit 150 may be installed at the oscillation portion 111 of the nanostructure 110 in a position where the amplitude of the oscillation portion 111 is maximized. The oscillation portion 111 of the nanostructure 110 oscillates due to external oscillation, and the width, height, and length of the oscillation portion 111 are denoted by "W", "t", and "l", respectively. The width "W" and height "t" of the oscillation portion 111 may range from several nm to 1 μm, and the length "l" may range from 100 nm to 100 μm.

The nanostructure 110 may be formed of one selected from the group consisting of Si, Ge, Sn, Se, Te, B, C, P, B—C, B—P(BP6), B—Si, Si—C, Si—Ge, Si—Sn, Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, BeSiN$_2$, CaCN$_2$ZnGeP$_2$, CdSnAs$_2$, ZnSnSb$_2$, CuGeP$_3$, CuSi$_2$P$_3$, (Cu,Ag)(Al, Ga, In, Ti, Fe)(S, Se, Te)$_2$, SiO$_2$, Si$_3$N$_4$, Ge$_3$N$_4$, Al$_2$O$_3$, (Al, Ga, In)$_2$(S, Se, Te)$_3$, Al$_2$CO, and combinations thereof. In order to oscillate the oscillation portion 111 of the nanostructure 110, piezoelectric devices are formed by depositing or sputtering a piezoelectric material or a metal material capable of oscillating the oscillation portion 111 on and under the oscillation portion 111. When a voltage is applied to the piezoelectric devices formed on and under the oscillation portion 111, the oscillation portion 111 oscillates in a vertical direction according to the extended length of the piezoelectric material formed on and under the oscillation portion 111 so that the oscillation portion 111 functions as an oscillator. Also, the oscillation portion 111 oscillates not only due to the piezoelectric material but also due to the controller 140. Specifically, when an alternating-current (AC) voltage is applied to the controller 140 to apply an AC electric field around the controller 140, charges of the sensing unit 150 and the oscillation portion 111 move in the direction of the AC electric field and attract charges of the controller 140, which have an opposite polarity to the charges of the sensing unit 150 and the oscillation portion 111. Also, when the polarity of the AC electric field applied to the controller 140 is reversed, the attraction of the sensing unit 150 and the oscillation portion 111 to the controller 140 becomes weak, so that the oscillation portion 111 is restored to its original position due to elasticity. Accordingly, the oscillation portion 111 continues to oscillate due to repeated AC oscillation. In this case, the cycle of the electric field applied to the controller 140 is equal to the mechanical resonance frequency of the nanostructure 110, resonance occurs so that the amplitude of the oscillation portion 111 is maximized. As a result, the controller 140 causes the oscillation of the oscillation portion 111 using the voltage applied through an electrode.

As shown in FIG. 2A, the mass spectrometer 100 may further include an external oscillation portion 230 disposed under the substrate 220. In this case, the entire substrate 220 can be oscillated using the external oscillation portion 230. The external oscillation portion 230 may be formed of a piezoelectric material, such as lead-zirconate-titanate (PZT) or quartz. Alternatively, the external oscillation portion 230 may be omitted as shown in FIG. 2B. In this case, the oscillation of the oscillation portion 111 is caused using the piezoelectric devices formed on and under the oscillation portion 111. When the external oscillation portion 230 is further disposed as shown in FIG. 2A, the oscillation of the oscillation portion 111 may be caused using the piezoelectric devices formed on and under the oscillation portion 111 or by provoking the oscillation of the entire substrate 220 using the external oscillation portion 230. Furthermore, in both cases shown in FIGS. 2A and 2B, the oscillation of the oscillation portion 111 may be induced using the controller 140.

The above-described mass spectrometer 100 can perform its functions based on the following principles. In the mass spectrometer 100, since an oscillation-causing material, such as PZT, is deposited on and under the oscillation portion 111 of the nanostructure 110, a mass variation can be sensed by oscillating the oscillation portion 111 due to the oscillation-causing material. As shown in FIGS. 2A and 2B, it is obvious that the oscillation of the oscillation portion 111 may be caused in various modes by variously combining the controller 140, the piezoelectric devices formed on and under the oscillation portion 111, and the external oscillation portion 230. The resonance frequency of the oscillation portion 111 of the nanostructure 110 of the mass spectrometer 100 shown in FIGS. 2A and 2B is determined by the length "l", width "W", and height "t" of the oscillation portion 111 and the density and Young's modulus of the nanostructure 110.

That is, the resonance frequency of the nanostructure 110 is as shown in Equation 1:

$$\omega_o = 2\pi(1.05)\sqrt{\frac{\varepsilon}{\rho}}\frac{t}{l^2} \qquad \text{[Equation 1]}$$

wherein $\varepsilon$ denotes the Young's modulus of the nanostructure 110, $\rho$ denotes the density of the nanostructure 110, "t" denotes the height of the oscillation portion 111, and "l" denotes the length of the oscillation portion 111. In general, a mass variation is closely associated with a frequency variation as shown in Equation 2:

$$\delta M = -2\frac{M_{\mathit{eff}}}{\omega}\delta\omega_o \qquad \text{[Equation 2]}$$

wherein $M_{eff}=0.735$ ltwρ. In other words, the mass spectrometer 100 according to the present embodiment is capable of mass analysis using the floated nanostructure 110 based on Equation 2.

As shown in Equation 1, the resonance frequency $\omega_o$ increases in inverse proportion to the square of the length "l" of the oscillation portion 111. Thus, it can be seen that as the length "l" of the oscillation portion 111 of the nanostructure 110 increases, the resonance frequency $\omega_o$ decreases. For example, when the length "l" of the oscillation portion 111 is several μm, the nanostructure 110 has a resonance frequency $\omega_o$ of several MHz. When the resonance frequency $\omega_o$ of the nanostructure 110 is several MHz, the mass spectrometer 100 has a sensitivity of several attograms (ag) or more. Accordingly, the mass spectrometer 100 according to the present embodiment can measure small amount of the material according to a resonance frequency variation even a single strand DNA. As a result, the mass spectrometer 100 can be applied to devices capable of sensing fine-mass materials, such as DNA, bio-materials including protein, and gas.

FIGS. 3 through 5 are cross-sectional views of the mass spectrometer 100 shown in FIG. 1, wherein the oscillation portion 111 enters an oscillation mode to sense a mass variation.

Referring to FIGS. 3 through 5, when the floated oscillation portion 111 is in a basic oscillation mode, the material 210 is adsorbed to the sensing unit 150 prepared in a region of the oscillation portion 111. In general, the oscillation portion 111 oscillates in the same way as a string having both ends fixed. Of course, it is possible that the oscillation portion 111 oscillate in more complicated and various oscillation modes or a nonlinear oscillation mode, as opposed to the oscillation mode shown in FIGS. 3 through 5.

In the present embodiment, when the material 210 is adsorbed to the sensing unit 150 and a mass variation of the oscillation portion 111 is sensed by the sensing unit 150, the oscillation mode of the oscillation portion 111 is varied. That is, the resonance frequency of the oscillation portion 111 is varied. In oscillation modes 310*a* and 310*b* shown in FIG. 3, the sensitivity of the sensing unit 150 can be maximized at a maximum-amplitude portion (i.e., the material 210) of the oscillation portion 111. Specifically, when an electrode for depositing a desired material is formed or a reactive region capable of reacting with a specific material is formed using chemical surface-processing or a specific reactant at the maximum-amplitude portion (i.e., the material 210) of the sensing unit 150, the sensing unit 150 reacts with the electrode or the reactive region so that the sensitivity of the sensing unit 150 can be maximized. When the mass of a portion of the material 210 is varied at the maximum-amplitude portion (i.e., the material 210), variations in resonance frequency, Q-factor, and phase shift can be maximized. This is because the frequency and Q-factor must be very high in order to sense the variations in the resonance frequency and Q-factor without any noise. Also, it is the best way to read the variations in the resonance frequency and Q-factor at the maximum-amplitude portion (i.e., the material 210) in order to exactly analyze mass. That is, even if a material is adsorbed to a low-amplitude portion, since the material does not affect the entire amplitude, sensing the mass variation of the oscillation portion 111 by sensing the variation in the resonance frequency becomes difficult.

For example, when the sensing unit 150 formed of platinum (Pt) is hydrogenated, hydrogen (H) is adsorbed on the surface of the sensing unit 150. Thus, the resonance frequency and Q-factor of the oscillation portion 111 depend on whether H is adsorbed or not. That is, in the present embodiment, the variation in the resonance frequency and Q-factor of the oscillation portion 111 can be sensed using the amount of H adsorbed to the sensing unit 150.

As another example, when the sensing unit 150 is formed of gold (Au) and a material obtained by thiol linked DNA, thiol combines with Au to form a single-strand DNA probe. In this case, the mass is measured using the above-described method. If target DNA, which combines with an anchored single-strand DNA, is supplied and complementarily bonded with the single-strand DNA probe, the mass of the hybridized DNA is also varied. Based on the above-described principles, the mass spectrometer 100 can function not only as a bio-material sensor but also as a bio-sensor using protein antigen-antibody interaction.

In order to manufacture devices with maximum sensitivity, such as the bio-material sensor and the bio-sensor, as shown in FIGS. 3 through 5, the sensing unit 150 to which the material 210 is adsorbed may be formed at the maximum-amplitude portion of the oscillation portion 111, and the sensing unit 150 may be formed of a material that reacts with a target material. In addition, as shown in FIGS. 3 through 5, the oscillation portion 111 may enter various oscillation modes 310*a*, 310*b*, 410*a*, 410*b*, 510*a*, and 510*b*. Meanwhile, the material 210 may be adsorbed to the sensing unit 150 using various methods, for example, a deposition process, a sputtering process, an electrochemical adsorption process, and a simple chemical reaction.

FIG. 6A is a perspective view of a 3D sensor including a plurality of nanostructures and a laser sensing unit according to another exemplary embodiment of the present invention, and FIG. 6B is a partial scanning electron microscope (SEM) image of the 3D sensor shown in FIG. 6A.

Referring to FIGS. 6A and 6B, a 3D sensor 600 including a plurality of nanostructures 110 can measure the sensitivity of a material using a laser source 610 and a laser sensing unit 620 for sensing a laser beam 630. The 3D sensor 600 includes a substrate 220, an insulating layer 130, a plurality of electrodes 141, the plurality of nanostructures 110, sensing units 150, the laser source 610, and the laser sensing unit 620. The insulating layer 130 is disposed on the substrate 220. The plurality of electrodes 141 are disposed on the insulating layer 130 parallel to one another. The plurality of nanostructures 110 intersect the electrodes 141 in a matrix shape and float over the substrate 220. At least one sensing unit 150 is disposed on each of the nanostructures 110. The laser source 610 irradiates the laser beam 630 in order to measure variations of the resonance frequency of the nanostructures 110. Also, the laser sensing unit 620 senses the laser beam 630 that is incident from the laser sensing unit 610, reflected from the nanostructure 110. When the laser beam 630 irradiated by the laser source 610 to an oscillation portion is reflected and sensed by the laser sensing unit 620, the 3D sensor 600 senses a variation in the light intensity of the laser beam 630 sensed by the laser sensing unit 620 to analyze the mass of the material. Therefore, the 3D sensor 600 senses the variation in the light intensity by sensing variations in frequency, phase change, and Q-factor. In other words, when a material with predetermined mass is adsorbed to the sensing unit 150, a resonance frequency is varied and thus, the light intensity of the laser beam 630 incident to the laser sensing unit 620 is also varied. Specifically, the frequency of the incident laser beam 630 may be scanned. In this case, when the frequency of the incident laser beam 630 is equal to the resonance frequency, the largest photocurrent is supplied and a phase change is maximized. As a result, the resonance frequency can be obtained, and a mass variation can be determined by a difference between the resonance frequency obtained when the material with the mass is adsorbed and a resonance frequency obtained when the material with the mass is not adsorbed. In other words, the mass variation can be determined by sensing the phase change and the variation in Q-factor, and resonance frequency.

More specifically, each of the nanostructures 110 includes a linear oscillation portion 111 floated three-dimensionally over the substrate 220 and support portions 112 disposed on both ends of the oscillation portion 111. At least one sensing unit 150 may be installed on the oscillation portion 111 of the nanostructure 110. The oscillation portion 111 of the nanostructure 110 oscillates due to external vibration and has a width "W", a height "t", and a length "l". The oscillation portion 111 may be formed to a length "l" of about 100 nm to 100 μm.

The nanostructures 110 may be formed of one selected from the group consisting of Si, Ge, Sn, Se, Te, B, C, P, B—C, B—P(BP6), B—Si, Si—C, Si—Ge, Si—Sn, Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, $BeSiN_2$, $CaCN_2ZnGeP_2$, $CdSnAs_2$, $ZnSnSb_2$, $CuGeP_3$, $CuSi_2P_3$, $(Cu,Ag)(Al, Ga, In, Ti, Fe)(S, Se, Te)_2$, $SiO_2$, $Si_3N_4$, $Ge_3N_4$, $Al_2O_3$, $(Al, Ga, In)_2(S, Se, Te)_3$, $Al_2CO$, and combinations thereof.

The 3D sensor having the above-described structure may be manufactured using the following process. FIG. 6B illustrates a silicon on insulator (SOI) substrate (not shown). The insulating layer 130 is formed of silicon oxide on the SOI substrate, and a support 120 is also formed of silicon oxide on the insulating layer 130. An uppermost silicon layer having a desired shape, which is formed on the substrate, is etched, thereby forming the nanostructure 110 that includes the oscillation portion 111 formed of silicon and floating over the substrate and the support portions 112 prepared on both ends of the oscillation portion. Thereafter, silicon oxide formed under the nanostructure 110 is removed by etching to form the support 120 in the same structure as the support portion 112 of the nanostructure 110. After that, the sensing unit 150 is formed to bond a desired chemical or biochemical material to the floated nanostructure 111. Next, a metal material is deposited on the substrate having the insulating layer 130, thereby forming a plurality of electrodes 141 that cause the oscillation of the oscillation portion 111 along with the sensing unit 150. As a result, the manufacture of the 3D sensor 600 may be completed.

In the 3D sensor 600 obtained using the above-described process, the laser beam 630 irradiated by the laser source 610 is reflected by the sensing unit 150 prepared on the oscillation portion 111 and travels toward the laser sensing unit 620. In this case, the light intensity of the laser beam 630 is varied according to resonance of the oscillation portion 111 and affects the amplification of a signal of the laser sensing unit 620. Thus, the resonance of the oscillation portion 111 is sensed by sensing the amplification of the signal of the laser sensing unit 620. When a sensing target material is contained in a microcapsule surrounding a fluid, the sensitivity of the sensing target material can be elevated by means of electrophoresis using the electrodes 141. Specifically, when an AC or DC electric field is applied to the electrode 141, the sensing target material contained in the fluid is pulled toward the sensing unit 150 due to the electric field, so that density becomes higher near the sensing unit 150. As a result, the sensitivity of the sensing target material contained in the fluid can be elevated.

FIG. 7 is a schematic diagram of a plurality of nanostructures including oscillation portions with different lengths.

Referring to FIG. 7, a 3D sensor according to the present embodiment includes a substrate (not shown) including an insulating layer 130, a plurality of electrodes 141 disposed on the substrate, supports 120 disposed on the substrate to support nanostructures 710, 720, 730, 740, and 750, the nanostructures 710, 720, 730, 740, and 750, which are supported by the supports 120 and float over the substrate, and sensing units 150 disposed on the respective nanostructures 710, 720, 730, 740, and 750. In the present embodiment, the nanostructures 710, 720, 730, 740, and 750 include oscillation portions 711, 721, 731, 741, and 751 and support portions 712, 722, 732, 742, and 752, respectively. The oscillation portions 711, 721, 731, 741, and 751 have different lengths so that the oscillation portions 711, 721, 731, 741, and 751 have respectively different resonance frequencies.

The oscillation portions 711, 721, 731, 741, and 751 having different resonance frequencies can be used for various mass spectrometers and sensors because when searching for resonance frequencies by varying frequencies, resonance occurs at several portions. Also, when the oscillation portions 711, 721, 731, 741, and 751 have different resonance frequencies, different sensors may be attached to respectively different portions using probes formed of different materials to form a sensor array.

FIG. 8A is a schematic diagram of a molecular sensor using nanostructures according to an exemplary embodiment of the present invention, and FIG. 8B is an enlarged view of region "A" shown in FIG. 8A.

Referring to FIG. 8A, the molecular sensor includes a controller 140 disposed on a substrate and a nanostructure 110 floating over the controller 140. The nanostructure 110 includes a linear oscillation portion 111 and support portions 112 prepared on both ends of the oscillation portion 111 to support the oscillation portion 111. A support 120 is disposed under each of the support portions 112 of the nanostructure 110 and supports the nanostructure 110. Referring to FIG. 8B, a sensing unit 150 for sensing a material supplied to a maximum-amplitude portion is disposed on the oscillation portion 111. At least one probe 810a is prepared on the sensing unit 150 so that the supplied material may be adsorbed to the probe 810a. A target material 810b, such as an external fluid, is adsorbed onto the probe 810a. The nanostructure 110 having the above-described structure can be utilized as a sensor by sensing a variation in the mass of the material 810b adsorbed to the probe 810a. The sensing unit 150 may be formed of metal, silicon, oxide, or crystal thereof. The metal may be gold (Au), platinum (Pt), or silver (Ag), and the oxide may be silicon oxide, zinc oxide, aluminum oxide, or titanium oxide. Here, the crystal is limited to a non-oxide crystal, such as a silicon crystal or a titanium crystal, or an non-amorphous oxide crystal. Also, an organic probe (not shown) may be prepared on the probe 810a. The organic probe formed on the probe 810a may be formed of a thiol group, an amine group, a silane group, DNA combined with the thiol group, the amine group, or the silane group, or an antibody. The organic probe may be chemically combined with a material adsorbed thereto.

FIG. 9 illustrates the layout of a plurality of nanostructures including oscillation portions with different lengths, FIG. 10 is a view showing the construction of an apparatus using the nanostructures shown in FIG. 9 as bio-sensors, chemical sensors, or gas sensors, and FIG. 11 is an enlarged view of region "B" shown in FIG. 10.

The apparatus shown in FIG. 10 has a structure to generally isolate an internal material from the outside. The apparatus includes a bottom portion 1010, a plurality of nanostructures 110, a plurality of supports 120, a lateral portion 1020, a top portion 1030, a fluid inlet port 1060, and a fluid outlet port 1070. The bottom portion 1010 supports and hermetically seals the apparatus. The nanostructures 110 are formed on the bottom portion 1010 and function as sensors. The supports 120 support the nanostructures 110. The lateral portion 1020 is formed in an outer circumferential direction of the bottom portion 1010. The top portion 1030 is disposed on the lateral portion 1020 and covers the nanostructures 110. The fluid inlet port 1060 is formed in a region of the lateral portion 1020, and the fluid outlet port 1070 is formed in another region of the lateral portion 1020. A laser unit 1040 and a laser sensing unit are installed over the top portion 1030. The laser unit 1040 irradiates laser beams to the nanostructures 110, and the laser sensing unit 1050 senses laser beams reflected by the nanostructures 110. The laser unit 1040 is a semiconductor laser.

Referring to FIG. 11, which enlarges the region "B" shown in FIG. 10, a plurality of nanostructures 110 function as sensors and have oscillation portions 111 with different lengths. At least one sensing unit 1130 is prepared on each of the oscillation portions 111 to sense a fluid or materials supplied to the apparatus. The sensing units 1130 installed on each of the oscillation portions 111 may be provided in various shapes and numbers. When a fluid is supplied via the fluid inlet port 1060 of FIG. 10 and brought into contact with the sensing unit 1130 prepared on the oscillation portion 111 of the nanostructure 110, the resonance frequency of the oscillation portion 111 is measured using a laser source 1110. Also, when a sensing target material 1120 reacts with the sensing unit 1130, a variation in the resonance frequency of the oscillation portion 111 is measured. That is, when the material 1120 is adsorbed to the sensing units 1130 formed at maximum-amplitude portions of the oscillation portions 111 having different resonance frequencies, the oscillation frequencies of the oscillation portions 111 are varied. Thus, variations in the resonance frequency and Q-factor can be obtained using the laser source 1110, and the mass of the material 1120 can be detected based on the variations in the resonance frequency and Q-factor, phase shift.

Embodiment 2: 3D Electronic Device

In the present embodiment, a 3D electronic device will be described in detail. The 3D electronic device is an electronic device designed to occupy a 3D space and have a 3D structure. Specifically, the 3D electronic device according to the present embodiment may be obtained by improving the characteristics of a conventional molecular device or a conventional organic electronic device, which includes a field-effect transistor (FET), a single electron transistor (SET), or a molecular transistor.

In the present embodiment, the 3D electronic device includes nanostructures, which float over a substrate as in the embodiment 1, and source and drain electrodes, which are disposed near or under the nanostructures and electrically connected to the nanostructures. Alternatively, during formation of a SET, the amount of charge emitted to a channel is controlled using a gate electrode, and the energy level of the SET is controlled using another gate electrode. Alternatively, the single electron transistor is bonded with a FET that is manufactured using an additional process, thereby forming a SET-FET hybrid device.

FIG. 12 is a diagram of a SET using nanostructures according to another exemplary embodiment of the present invention.

Referring to FIG. 12, the SET according to the present embodiment includes a source electrode 1210 and a drain electrode 1220, which are disposed on a substrate and have a gap 1230 therebetween, and a nanostructure 1250, which floats over the source and drain electrodes 1210 and 1220 and functions as a gate electrode. The SET includes the gap 1230, which is formed in a region of the floated nanostructure 1250, specifically, between the source and drain electrodes 1210 and 1220, a gap formed between the source and drain electrodes 1210 and 1220 and a quantum dot 1240, and the quantum dot 1240 formed over the gaps. In the present embodiment, the nanostructure 1250 formed over the source and drain electrodes 1210 and 1220 functions as the gate electrode.

In the SET having the above-described construction, when the quantum dot 1240 is disposed in the nanostructure 1250 functioning as the gate electrode, a position of an energy level in the quantum dot 1240 is controlled using the gate electrode, i.e., the nanostructure 1250, thereby changing the amount of charge emitted from the source electrode 1210 to produce a transistor phenomenon. The above-described SET is an example of the simplest SET. In the present embodiment, a vacuum state or air is used as a tunneling barrier (or the gap 1230 between the source and drain electrodes 1210 and 1220). That is, there is no line that connects the source electrode 1210 with the quantum dot 1240, and an air resistance is recognized as a tunneling barrier (i.e., potentials).

FIG. 13 is a diagram of a 3D electronic device according to another exemplary embodiment of the present invention, which performs operations more actively than the SET shown in FIG. 12. Specifically, the SET of FIG. 12 operates using a native oxide layer disposed between the quantum dot 1240 and the nanostructure 1250, while the 3D electronic device of FIG. 13 further includes an insulating layer 1320 disposed on a nanostructure 1250 functioning as a gate electrode.

Referring to FIG. 13, the 3D electronic device includes a source electrode 1210 and a drain electrode 1220, a nanostructure 1250, supports 1310, and a pair of electrodes 1340. The source and drain electrodes 1210 and 1220 are disposed on a substrate (not shown) and have a gap 1230 therebetween. The nanostructure 1250 floats over the substrate. The supports 1310 are disposed under both ends of the nanostructure 1250 and support the nanostructure 1250. The pair of electrodes 1340 are formed on both ends of the nanostructure 1250 and connected to an external circuit. Also, the 3D electronic device further includes the insulating layer 1320, which surrounds the nanostructure 1250, and a sensing unit 1240 formed on an oscillation portion of the floated nanostructure 1250. For example, assuming that the floated nanostructure 1250 is formed of silicon, the insulating layer 1320 may be an oxide layer obtained using a thermal treatment.

When the nanostructure 1250 functioning as the gate electrode is manufactured using the above-described method, since the insulating layer 1320 surrounds the nanostructure 1250, the electrodes 1340 are further formed over the insulating layer 1320 in order to connect the 3D electronic device and the external circuit.

The structure shown in FIG. 13 can be applied not only to the SET of FIG. 13 but also to a spin device. For example, assuming that the source and drain electrodes 1210 and 1220 and the quantum dot 1240 are formed of magnetic materials, a spin type of a magnetic material disposed on the quantum dot 1240 may be shifted using the nanostructure 1250 functioning as the gate electrode. Specifically, when an AC or DC current is supplied to the nanostructure 1250, a spin direction of the magnetic material disposed on the quantum dot 1240 is shifted due to a magnetic field caused by the current supplied to the nanostructure 1250 and counteracts the magnetism of electrons emitted from the source electrode 1210. As a result, when the spin direction is the same, the conductivity of the 3D electronic device increases, and when the spin direction is different, the conductivity of the 3D electronic device decreases. Thus, the 3D electronic device can function as a spin device.

FIG. 14A is a view showing the construction of a 3D electronic device according to another exemplary embodiment of the present invention, wherein a molecular insulating layer or an organic insulating layer is deposited without using air and vacuum as tunneling potentials as in FIGS. 12 and 13.

Referring to FIG. 14A, the 3D electronic device includes a source electrode 1210, a drain electrode 1220, a gap 1230 formed between the source and drain electrodes 1210 and 1220, and a nanostructure 1250, which floats over the gap 1230, functions as a gate electrode, and is surrounded by a gate insulating layer 1320. The nanostructure 1250 is surrounded by the insulating layer 1320, and a quantum dot 1240 is formed in a region of the nanostructure 1250 surrounded by the insulating layer 1320. An organic insulating layer 1410 is formed of an organic material between the quantum dot 1240 and the gap 1230 formed between the source and drain electrodes 1210 and 1220. The organic insulating layer 1410 may be formed using a deposition process, a self-assembly process, or a spin coating process.

In general, since an organic material or other inorganic material has a higher dielectric constant than vacuum, the organic insulating layer 1410 or the molecular insulating layer is formed between the quantum dot 1240 and the gap 1230 as shown in FIG. 14A, thereby elevating a gate effect.

FIG. 14B is a view showing the construction of a 3D electronic device according to another exemplary embodiment of the present invention, wherein a transistor is driven by attaching a molecular and organic material or a nanodot material 1420 to at least a region of a gap 1230 formed between a source electrode 1210 and a drain electrode 1220.

Referring to FIG. 14B, charges that are transported via the source electrode 1210 to the drain electrode 1220 pass through the molecular or organic material or the nanodot material 1420 prepared in the region of the gap 1230 and reach the energy level of the molecular or organic material or the nanodot material 1420. In this case, the energy level of the molecular or organic material or the nanodot material 1420 is controlled using the nanostructure 1250 so as to drive the transistor. That is, the molecular or organic material or the nanodot material 1420 allows the charges to pass therethrough, and the nanostructure 1250 controls the charge amount of the molecular or organic material or the nanodot material 1420. An upper quantum dot 1240 may be removed to increase an electric field and effectively remove an energy level. Even if the upper quantum dot 1240 is provided, the energy level may be controlled. In this case, the gate insulating layer 1320 formed on the nanostructure 1250 functioning as the gate electrode may be an inorganic insulating layer, an organic insulating layer, air, or vacuum.

FIGS. 15 and 16 are views showing the constructions of a SET, a spin device, or a FET, which includes a nanostructure, according to exemplary embodiments of the present invention. Specifically, FIG. 15 illustrates the construction of a SET, a spin device, or a FET using an inorganic insulating layer, while FIG. 16 illustrates the construction of a SET, a spin device, or a FET using air and vacuum as an insulating layer.

Referring to FIG. 15, the SET, the spin device, or the FET is surrounded by an insulating layer 1320 and includes a nanostructure 1250 functioning as a gate electrode, an insulating layer 1510 disposed on a substrate, a gate insulating layer 1520, which is disposed under the nanostructure 1250 and has the same shape as the nanostructure 1250, and source and drain electrodes 1210 and 1220, which are formed across the gate insulating layer 1520. Since the structure of FIG. 15 has the same components as in FIG. 13 except for the gate insulating layer 1520, a description thereof will be omitted here. The gate insulating layer 1520 shown in FIG. 15 is formed of an inorganic material, specifically, the same material as the insulating layer 1510 or a different material from the insulating layer 1510. In particular, an insulating material, which is previously formed to manufacture a substrate sample, may be used as the gate insulating layer 1520. Since the structure of FIG. 16 also has the same components as in FIG. 13 except for a gate insulating layer 1610, a description thereof will be omitted here. In the structure shown in FIG. 16, air and vacuum are used as the gate insulating layer 1610.

FIG. 17A is a view showing the construction of a FET using air or a vacuum state as an insulating layer, according to another exemplary embodiment of the present invention, and FIG. 17B is an enlarged view of region "C" shown in FIG. 17A.

Referring to FIGS. 17A and 17B, the FET uses the air or vacuum state, which is described with reference to FIG. 16, as a gate insulating layer, and a gate 1740 is formed across a source electrode 1720 and a drain electrode 1730. The gate 1740 may be formed during the manufacture of a nanostructure functioning as a gate electrode. In other words, when the gate 1740 is formed to the same height as the floated nanostructure 1250, the FET can be driven using the insulating layer 1750 surrounding the nanostructure not to cause an electrical short. In this structure, the gate 1740 can control the circumference of a channel of the FET where conduction occurs.

FIG. 18 is a view showing the construction of a spin device, a FET, or a molecular device according to an exemplary embodiment of the present invention, wherein an insulating layer is formed of an inorganic material.

Referring to FIG. 18, the FET according to the present embodiment includes a gate insulating layer 1810, which supports a nanostructure under the floated nanostructure and has the same shape as the nanostructure. The structure shown in FIG. 18 prevents an upper channel from bending downward due to imbalance between gravity and tension, thereby inhibiting a variation in an electronic state.

FIG. 19 is a view showing the construction of a SET including a plurality of gates using an electric field, and FIG. 20 is a circuit diagram of the SET shown in FIG. 19.

In the SET, the flow of electrons in a channel 1330, which is disposed between source and drain electrodes and includes a nanostructure surrounded by a gate insulating layer, can be controlled using gate electrodes 1910, 1920, 1930, 1940, and 1950 shown in FIG. 19. For example, assuming that the channel 1330 is a p-type channel, when positive voltages are applied to the gate electrodes 1910, 1930, and 1950, no current flows due to the three voltages. In this case, portions of the channel 1330 disposed under the gate electrodes 1920 and 1940 function as two quantum dots both having isolated portions. In the above-described structure, the SET having two quantum dots can be formed. Also, when a plurality of gate electrodes are prepared, a plurality of SETs can be manufactured in equal number to the gate electrodes. In addition, when each of the gate electrodes is formed of a semiconductor material, each of the gate electrodes may function as a drain of a FET. As a result, the SET can be manufactured using the FET. Conversely, by forming a FET in the drain or source electrode of the SET, a SET-FET hybrid device can be manufactured. Referring to FIG. 20, capacitors C1, C2, C3, C4, and C5 may be prepared between the gate electrodes 1910, 1920, 1930, 1940, and 1950 and the channel 1330, respectively, and a power supply voltage and a ground voltage are respectively connected to both ends of the channel 1330. By controlling the capacitances of the capacitors C1, C2, C3, C4, and C5, the drive of the FET and SET can be varied.

While the invention has been shown and described with reference to certain exemplary embodiments thereof, it will be understood by those skilled in the art that various changes in form and details may be made therein without departing from the spirit and scope of the invention as defined by the appended claims.

The invention claimed is:

1. A three-dimensional (3D) nanodevice comprising:
at least one nanostructure, each nanostructure including an oscillation portion floating over a substrate and support portions for supporting both lengthwise end portions of the oscillation portion;
supports disposed on the substrate to support the support portions of each of the nanostructures;
at least one controller disposed at an upper portion of the substrate, a lower portion of the substrate, or both the upper and lower portions of the substrate to control each of the nanostructures; and
a sensing unit disposed on each of the oscillation portions to sense an externally supplied adsorption material.

2. The 3D nanodevice according to claim 1, further comprising an external oscillation portion disposed under the substrate.

3. The 3D nanodevice according to claim 1, wherein the controller includes a piezo-electric material or a metal material, which is disposed at an upper portion, a lower portion or both the upper and lower portions of the oscillation portion of the nanostructure to intersect the nanostructure and cause oscillation of the oscillation portion.

4. The 3D nanodevice according to claim 1, wherein the controller includes at least one electrode, which is disposed under the oscillation portion over the substrate to intersect the nanostructure and cause oscillation of the oscillation portion.

5. The 3D nanodevice according to claim 1, wherein the oscillation portion has a width of several nm to 1 µm, a height of several nm to 1 µm, and a length of 100 nm to 100 µm.

6. The 3D nanodevice according to claim 1, wherein each of the oscillation portion and the substrate is formed of one selected from the group consisting of Si, Ge, Sn, Se, Te, B, C, P, B—C, B—P(BP6), B—Si, Si—C, Si—Ge, Si—Sn, Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, $BeSiN_2$, $CaCN_2ZnGeP_2$, $CdSnAs_2$, $ZnSnSb_2$, $CuGeP_3$, $CuSi_2P_3$, $(Cu, Ag)(Al, Ga, In, Ti, Fe)(S, Se, Te)_2$, $SiO_2$, $Si_3N_4$, $Ge_3N_4$, $Al_2O_3$, $(Al, Ga, In)_2(S, Se, Te)_3$, $Al_2CO$, and combinations thereof.

7. The 3D nanodevice according to claim 1, wherein a plurality of nanostructures in which the lengths of the oscillation portions are the same as or different from each other are formed, or a plurality of nanostructures in which the lengths of the oscillation portions are partially the same as each other are formed.

8. The 3D nanodevice according to claim 7, wherein the oscillation portion uses resonance and nonlinear frequencies according to the length thereof.

9. The 3D nanodevice according to claim 8, wherein the sensing unit is formed at a maximum-amplitude region of the resonance frequency, and a probe for adsorbing a material is formed at the maximum-amplitude region.

10. The 3D nanodevice according to claim 9, wherein the sensing unit is formed of one selected from the group consisting of metal, silicon, and oxide.

11. The 3D nanodevice according to claim 10, further comprising an organic probe disposed on the sensing unit.

12. The 3D nanodevice according to claim 11, wherein the organic probe includes at least one selected from the group consisting of a thiol group, an amine group, a silane group, DNA combined with at least one of the thiol group, the amine group, and the silane group, and a bio-material containing an antibody and is chemically combined with the supplied material.

13. The 3D nanodevice according to claim 1, further comprising:
a lateral portion formed along a circumference of the substrate;
a fluid inlet port disposed in a first region of the lateral portion;
a fluid outlet port disposed in a second region of the lateral portion; and
a top portion disposed on the lateral portion.

14. The 3D nanodevice according to claim 13, further comprising:
a laser unit for irradiating laser beams to the oscillation portion of the nanostructure; and
a laser sensing unit for receiving the laser beams from the laser unit.

15. A three-dimensional (3 )nanodevice comprising:
at least one nanostructure, each nanostructure including an oscillation portion floating over a substrate and support portions for supporting both lengthwise end portions of the oscillation portion;
supports disposed on the substrate to support the support portions of the nanostructure;
at least one electrode disposed under the oscillation portion of the nanostructure to intersect the nanostructure; and
a sensing unit disposed on the oscillation portion to sense an externally supplied adsorption material.

16. The 3D nanodevice according to claim 15, wherein the nanostructure functions as a gate electrode.

17. The 3D nanodevice according to claim 16, wherein the electrode includes a source electrode and a drain electrode, and a gap is formed between the source and drain electrodes.

18. The 3D nanodevice according to claim 17, wherein a quantum dot is formed in the nanostructure over the gap formed between the source and drain electrodes.

19. The 3D nanodevice according to claim 17, wherein a quantum dot is formed in the nanostructure over the gap formed between the source and drain electrodes, and the source and drain electrodes are formed of a magnetic material.

20. The 3D nanodevice according to claim 17, wherein a plurality of gates are disposed over the substrate.

* * * * *